United States Patent [19]
Schanen et al.

[11] Patent Number: 6,081,576
[45] Date of Patent: Jun. 27, 2000

[54] SCALABLE DATA ACQUISITION SYSTEM

[75] Inventors: Paul C. Schanen, Waukesha; Thomas R. Murray, Delafield; Jonathan A. Murray, Sussex, all of Wis.

[73] Assignee: General Electric Company, Milwaukee, Wis.

[21] Appl. No.: 09/139,864

[22] Filed: Aug. 25, 1998

[51] Int. Cl.[7] .............................. A61B 6/03; G01N 23/04
[52] U.S. Cl. ............................................. 378/19; 378/901
[58] Field of Search ................................. 378/4, 15, 19, 378/901; 382/131

[56] References Cited

U.S. PATENT DOCUMENTS

| | | | |
|---|---|---|---|
| 5,737,382 | 4/1998 | Stierorfer | 378/19 |
| 5,867,554 | 2/1999 | Hupke | 378/4 |
| 5,991,357 | 11/1999 | Marcovici et al. | 378/19 |

*Primary Examiner*—David V. Bruce
*Attorney, Agent, or Firm*—Armstrong, Teasdale; Christian G. Cabou; Phyllis Y. Price

[57] ABSTRACT

A scalable data acquisition system (SDAS) that may be used in connection with both single slice and multislice imaging systems is described. Generally, the SDAS in configured for use in a computed tomography system and converts the low level electrical current signal from the x-ray detector to digital values for image reconstruction, display and archive. The SDAS also includes an anti-alias filter for each cell prior to analog to digital conversion (ADC). More specifically, the analog current signals from the detector are supplied to the SDAS input channels via shielded ribbon or flex cables. The cables are connected to the SDAS at the SDAS backplane. The SDAS Converter boards are also plugged into the SDAS backplane. This interconnection provides several advantages. For example, the backplane enables ganging the detector cells on the outside edges of the fan beam. The backplane also allows a redistribution of the detector cells to appropriate converter boards. Signals from more than one slice are contained in the same flex cable, and each converter board only serves one slice since the reconfiguration of SDAS from one multi-slice configuration to another or to the single slice configuration requires only the removal or addition of converter boards. Also, the backplane enables a blending or weaving of SDAS channels and detector cells near the end channels of a converter board. Artifacts such as a band in the image are usually the result of common or uniform error source across one group of adjacent channels versus a neighboring group of channels. If all the channels on one converter board have a common error difference compared to a neighboring converter board, this type of image artifact is quite likely. By interweaving detector cell assignments versus converter card on the edges of the converter card, the susceptibility to a band artifact is reduced.

30 Claims, 17 Drawing Sheets

| HELICAL | THICKNESS (mm) | | | | | |
|---|---|---|---|---|---|---|
| | 1.25 | 2.50 | 3.75 | 5.00 | 7.50 | 10.00 |
| | SCAN MODE | | | | | |
| | HI-Q | HI-SPEED | | | | |
| | SPEED (mm/rot) | | | | | |
| | 3.75 | 7.50 | 11.25 | 15.00 | 22.50 | 30.00 |
| AXIAL | THICKNESS (mm) | | | | | |
| | 1.25 | 2.50 | 3.75 | 5.00 | 7.50 | 10.00 |
| | NUMBER OF IMAGES PER ROTATION | | | | | |
| | 1i | 2i | 4i | | | |

FIG. 3

SCALABLE DATA ACQUISITION SYSTEM

BACKGROUND OF THE INVENTION

This invention relates generally to imaging and, more particularly, to scalable multislice imaging systems.

In at least some imaging systems generally referred as computed tomography (CT) systems, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodiodes adjacent the scintillator.

The detector typically is coupled to a data acquisition system which converts the analog signals output by the detector into digital form. In a scalable multislice imaging system, it would be desirable to provide a data acquisition system which can be easily and simply operated to collect one, two, or more slices of data. Such system also should enable fast scanning speeds with good image quality, z-axis resolution, and a low x-ray tube load.

BRIEF SUMMARY OF THE INVENTION

These and other objects may be attained by a scalable data acquisition system that may be used in connection with both single slice and multislice systems. A multislice system includes, in an exemplary embodiment, a scalable multislice detector, the scalable data acquisition system (SDAS), scalable scan management, control, and image reconstruction processes, and scalable image display and analysis. As used herein, the term scalable generally means that an operator can readily and simply select the desired number of slices and the slice thickness for images to be displayed.

Generally, the SDAS converts the low level electrical current signal from the x-ray detector to digital values for image reconstruction, display and archive. The SDAS also includes an anti-alias filter for each cell prior to analog to digital conversion (ADC). SDAS cells are typically referred to as channels. Detector cells can be ganged or paralleled to one SDAS channel. The ganging reduces spatial resolution. On the outer edges of the fan beam this resolution loss is not an application limitation and allows the production of detector cells of the same size throughout the detector. An advantage of ganging is a reduction in the number of required SDAS channels and the associated cost. The digital output from the SDAS is usually transmitted either in a serial or semi-serial fashion, as described below in more detail, to reduce the amount of interconnecting hardware.

The analog current signals from the detector are supplied to the SDAS input channels via shielded ribbon or flex cables. The cables are connected to the SDAS at the SDAS backplane. The SDAS Converter boards are also plugged into the SDAS backplane. This interconnection provides several advantages. For example, the backplane enables ganging the detector cells on the outside edges of the fan beam. The backplane also allows a redistribution of the detector cells to appropriate converter boards. Signals from more than one slice are contained in the same flex cable, and each converter board only serves one slice since the reconfiguration of SDAS from one multi-slice configuration to another or to the single slice configuration requires only the removal or addition of converter boards. Also, the backplane enables a blending or weaving of SDAS channels and detector cells near the end channels of a converter board. Artifacts such as a band in the image are usually the result of common or uniform error source across one group of adjacent channels versus a neighboring group of channels. If all the channels on one converter board have a common error difference compared to a neighboring converter board, this type of image artifact is quite likely. By interweaving detector cell assignments versus converter card on the edges of the converter card, the susceptibility to a band artifact is reduced.

Another aspect of the SDAS is that converter cards combine the anti-alias filter and ADC on the same board rather on separate boards. Having the filter and ADC on the same board enables the modularity required for the scalable DAS. The integrated filter-ADC function on the same board also limits the possibility of electromagnetic and conducted interference because of short electrical lead lengths.

Yet another aspect of the SDAS is the use of serial data transmission between converter boards dedicated to a particular slice. Adding more slices thus simply adds more serial data streams. The SDAS uses a daisy-chain serial bus, but a broadcast bus could be used. The advantage of the daisy-chain bus is the shortness of lead lengths for the transmitted signals. Short lead length enables use of less robust and expensive drivers. The daisy chain bus is a buffering and retransmission of the received data, with the data from the receiving board being inserted in-time in front of the received data.

The above described scalable data acquisition system can be easily and simply operated to collect one, two, or more slices of data. Specifically, the SDAS can be reconfigured by adding or removing printed circuit boards to accommodate the number of slices provided by the detector. Such system also enables fast scanning speed with good image quality, z-axis resolution, and a low x-ray tube load.

BRIEF DESCRIPTION OF THE DRAWINGS

FIG. 3 is an exemplary embodiment of a scan user interface than can be used in conjunction with the system illustrated in FIGS. 1 and 2.

DETAILED DESCRIPTION OF THE INVENTION

The scalable data acquisition system (SDAS) is described herein in connection with an exemplary multislice CT system. The SDAS, however, is not limited to practice with one particular imaging system and can be used in connection with many other systems. For example, although one particular detector is described, other detectors could be used in connection with the SDAS, and the SDAS is not limited to practice with any one particular type of detector. Specifically, the detector described below includes a plurality of modules and each module includes a plurality of detector cells. Rather than the specific detector described below, a detector which has non-segmented cells along the z-axis, and/or a detector which has multiple modules with multiple elements along the x-axis and/or z-axis joined together in either direction to acquire multislice scan data simultaneously, can be utilized. Generally, the system is operable in single slice or multislice modes to collect 1 or more slices of data. Axial and helical scans can be performed with the system, and cross section images of a scanned object can be processed, reconstructed, displayed and/or archived.

Figure 1:
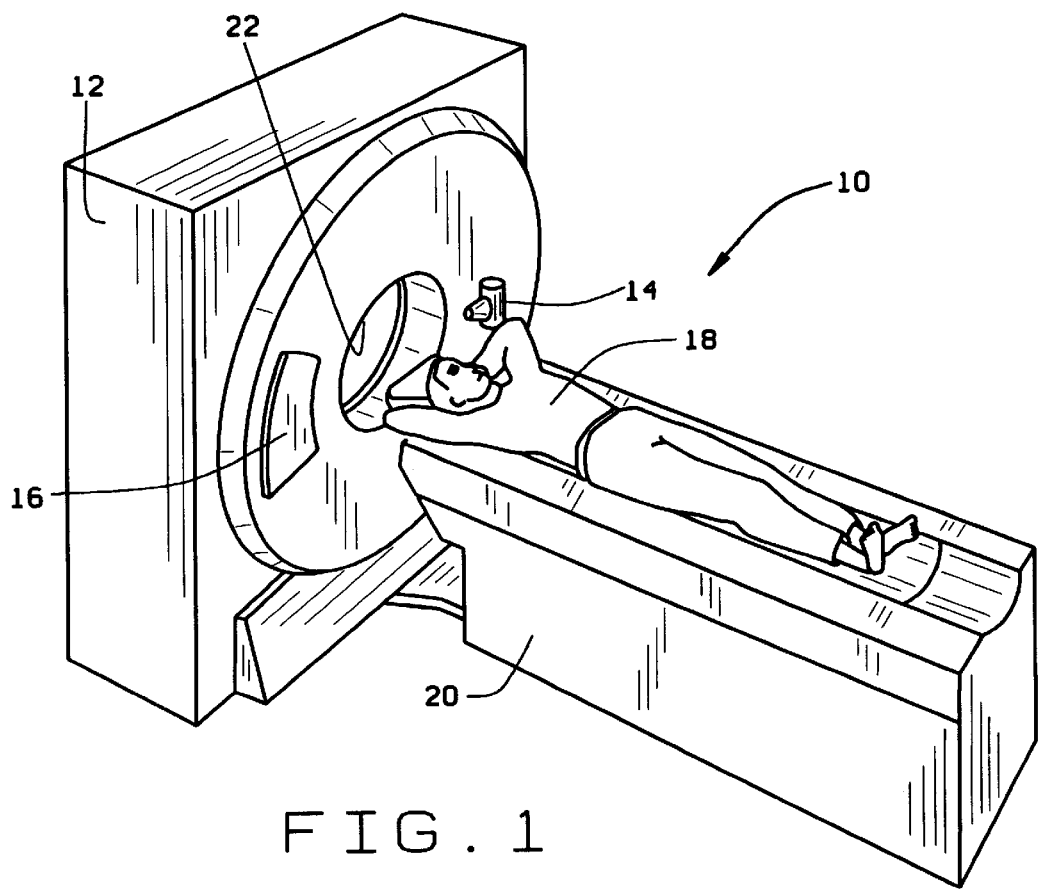
FIG. 1 is a pictorial view of a CT imaging system.

Referring now specifically to FIG. 1, a computed tomography (CT) imaging system 10 is shown as including a gantry 12 representative of a "third generation" CT scanner. Gantry 12 has an x-ray source 14 that projects a beam of x-rays toward a detector array 16 on the opposite side of gantry 12. Detector array 16 is formed by a plurality of detector modules which together sense the projected x-rays that pass through a medical patient 18. Each detector module produces an electrical signal that represents the intensity of an impinging x-ray beam and hence the attenuation of the beam as it passes through patient 18.

During a scan to acquire x-ray projection data, gantry 12 and the components mounted thereon rotate about a center of rotation. A motorized table 20 positions patient 18 relative to gantry 12. Particularly, table 20 moves portions of patient 18 through a gantry opening 22 during a scan.

Figure 2:
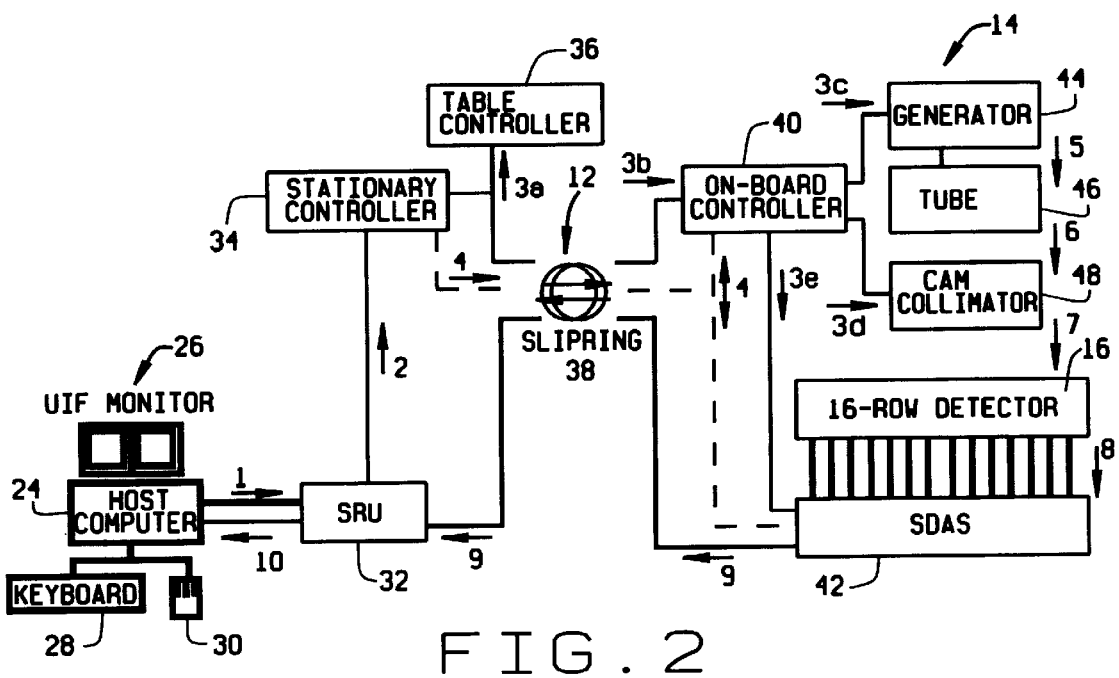
FIG. 2 is a block schematic diagram of the system illustrated in FIG. 1.

FIG. 2 is a block schematic diagram of the system illustrated in FIG. 1. As shown in FIG. 2, system 10 includes a host computer 24 coupled to a monitor (user interface) 26 for displaying images and messages to an operator. Computer 24 also is coupled to a keyboard 28 and a mouse 30 to enable the operator to input information and commands to computer 24. Computer 24 is coupled to a scan and reconstruction control unit (SRU) 32. SRU 32 also includes image generation controls. In one specific embodiment, SRU 32 includes a SGI PCI-based central processing unit which operates on an IRIX operating system. SRU 32 also includes an interface processor for interfacing with the data acquisition system (described below), and a scan data correction digital signal processing board for performing preprocessing, which is known in the art. SRU 32 further includes an image generator for filtered backprojection and postprocessing operations, as is known in the art.

A stationary controller 34 is connected to SRU 32, and controller 34 is coupled to a table controller 36. Stationary controller 34 also is connected, through a slipring 38, to an on-board controller 40 and a scalable data acquisition system (SDAS) 42. Slipring 38 enables contactless transmission of signals across the slipring boundary and supports the necessary bandwidth for transmission of data and commands across the boundary. SDAS 42 samples and acquires the data from detector 16 and converts the sampled analog signals to digital signals. SDAS 42, in one specific embodiment, includes forty eight interchangeable converter cards to support four row data acquisition. For two row data acquisition, twenty four cards could be used. In one specific embodiment, there are sixty four input channels per converter card and 1408 Hz sampling can be performed. SDAS 42 also includes a front-end pre-amplifier for amplifying the signals. Further details regarding SDAS are set forth below.

On-board controller 40 controls operation of x-ray source 14 and operation of SDAS 42. X-ray source 14 includes a high voltage generator 44 coupled to an x-ray tube 46. Tube 46 may, for example, be the tube known in the art is the Gemini-1 tube and currently utilized in at least some CT system commercially available from General Electric Company, Milwaukee, Wis., 53201. Beams projected by X-ray tube 46 pass through a prepatient cam collimator 48 and impinge upon detector 16 (illustrated as a 16 row detector). Cam collimator 48 also is controlled by on-board controller 40. Outputs from detector 16 are supplied to SDAS 42.

In FIG. 2, data flow is illustrated by bold lines, control flow is illustrated by normal lines, and real-time control flow is illustrated by dotted lines. The numeric identifiers associated with the flows are set forth below.

1: scan and reconstruction prescription from operator
  2: scan prescription to "master" controller
  3: scan parameters distributed
    3a: table position
    3b: rotating parameters
    3c: kV and mA selections
    3d: x-ray beam collimation and filter selections
    3e: detector slice thickness and SDAS gain selections
  4: real-time control signals during scanning
  5: high voltage
  6: un-collimated x-ray beam
  7: collimated x-ray beam
  8: analog scan data
  9: digital scan data
  10: patient images Rotation of gantry 12 and the operation of x-ray source 14 are governed by controller 34. On-board controller 40, under the control of stationary controller 34, provides power and timing signals to x-ray source 14. SDAS 42 samples analog data from detector 16 and converts the data to digital signals for subsequent processing. SRU 32 receives sampled and digitized x-ray data from SDAS 42 and performs high speed image reconstruction. The reconstructed image is applied as an input to computer 24 which stores the image in a mass storage device.

Computer 24 also receives commands and scanning parameters from an operator via keyboard 28 and mouse 30. Monitor 26 allows the operator to observe the reconstructed image and other data from computer 24. The operator supplied commands and parameters are used by computer 24 to provide control signals and information. In addition, controller 36 controls motorized table 20 to position patient 18 (FIG. 1).

Generally, the above described CT system is operable to collect 1, 2 or more slices data. Axial and helical scans can be performed with the system, and cross section images of a scanned object can be processed, reconstructed, displayed and/or archived. Scalable axial image reconstruction and display refers, for example, to selectability of the image thickness, number of slices, and number of images to be displayed. Further, the system is not limited to practice with any one particular image reconstruction algorithm, and it is contemplated that many different reconstruction algorithms can be utilized. Exemplary algorithms are set forth in U.S. Pat. Nos. 5,469,487, 5,513,236, 5,541,970, 5,559,847, and 5,606,585, and in co-pending U.S. patent application Ser. No. 08/561,382 (filed Nov. 21, 1995), Ser. No. 08/779,961 (filed Dec. 23, 1996), and Ser. No. 08/797,101 (filed Nov. 26, 1997), all of which are assigned to the present assignee, and all of which are incorporated herein, in their entirety, by reference.

In the axial multi-slice scan mode, multiple rows of scan data can be processed before image reconstruction, and the data can be used to produce either multiple thin slices or a reduced number of thicker slices with reduced image artifact. In addition, images with thicker slice thicknesses can be later reconstructed retrospectively into thinner slices of images based on clinical diagnosis needs. As a result, the number of unwanted images for viewing, filming, and archiving is reduced. In addition, high z-axis resolution images can be later reconstructed for patient diagnosis.

Exemplary axial multi-slice modes are set forth below in Table 1.

TABLE 1

| Acquisition Image Thickness & Mode | | Retrospective Reconstruction Image Thickness Available |
|---|---|---|
| 1.25 mm | 4i | 1.25, 2.5, 5 mm |
| 2.5 mm | 2i | 1.25, 2.5, 5 mm |
| 2.5 mm | 4i | 2.5, 5, 10 mm |
| 3.75 mm | 4i | 3.75, 7.5 mm |
| 5 mm | 1i | 1.25, 2.5, 5 mm |
| 5 mm | 2i | 2.5, 5, 10 mm |
| 5 mm | 4i | 5, 10 mm |
| 7.5 mm | 2i | 3.75, 7.5 mm |
| 10 mm | 1i | 2.5, 5, 10 mm |
| 10 mm | 2i | 5, 10 mm |

As one specific example, and for an axial mode acquisition for a 2.5 mm image thickness in the 2i mode, several retrospective reconstruction options that can be selected. For example, 4 images having a slice thickness of 1.25 mm can be reconstructed, 2 images having a slice thickness of 2.5 mm can be reconstructed, and 1 image having a slice thickness of 5 mm can be reconstructed. Accordingly, more images (e.g., 4 images) having a thinner slice thickness can be retrospectively reconstructed than the mode (i.e., 2i) in which the scan was performed. In addition, fewer images (e.g., 1 image) having a thicker slice thickness can be retrospectively reconstructed than the mode in which the scan was performed.

Further, and with respect to archiving images, the system enables storage of fewer images which require less storage space. For example, if 20 mm of patient anatomy is scanned in the 2i mode, 80 images can be generated. Storing 80 images for 20 mm of patient anatomy requires a large amount of memory. It is often the case that high resolution is not required for the entire 20 mm of patient anatomy. For example, it may be that only about 5 mm of the anatomy requires such high resolution. Using the data collected in 2.5 mm thickness 2i mode scan, the operator can retrospectively reconstruct images having a thickness of 5 mm for the majority of the anatomy, and thinner image slices (e.g., 1.25 mm) only at the locations where higher resolution is required. Using this retrospective reconstruction, the number of images to be archived can be significantly reduced.

Selection of the above described retrospective reconstruction is provided through the user interface, and possible because the scan data is collected using a multislice detector which is described below in more detail. With the thin slice scan data available, the operator can select from many different slice thicknesses when performing retrospective reconstruction.

In the helical multi-slice scan mode, multiple combinations of patient table speed and x-ray beam and detector collimations, enable generation of images having different z-axis resolution can be produced. For example, at the table speed of 30 mm/rotation, images of 5–10 mm slices can be generated. Thicker slice (such as 10 mm) images can be generated prospectively, which provides the benefit of a reduced number of images and reduced image reconstruction time. At a later time, thinner slice images can be generated retrospectively using the same data. Such thinner slice images may be necessary depending on the clinical application needs and can be generated without rescanning the patient.

Exemplary helical multi-slice modes are set forth below in Table 2.

TABLE 2

| Table Speed (mm / rotation) | | Retrospective Reconstruction Image Thicknesses Available |
|---|---|---|
| Hi-Q Scan Mode | Hi-Speed Scan Mode | |
| 3.75 | 7.5 | 1.25, 2.5 mm |
| 7.5 | 15 | 2.5, 3.75, 5 mm |
| 11.25 | 22.5 | 3.75, 5, 7.5 mm |
| 15 | 20 | 5, 7.5, 10 mm |

For example, in a high quality image (Hi-Q) scan mode of 3.75 mm/rotation (i.e., the patient table moves 3.75 mm for each gantry rotation), or in a high speed (Hi-Speed) scan mode of 7.5 mm/rotation, images having slice thicknesses of 1.25 mm and 2.5 mm can be reconstructed retrospectively. As with the axial multi-slice mode, many other alternatives are possible depending upon the particular construction of the system components. Again, such flexibility in retrospective reconstruction provides many advantages including enabling the generation of images having the necessary resolution yet reducing the memory necessary for storing the desired images.

FIG. 3 is an exemplary embodiment of a scan user interface than can be used in conjunction with the system illustrated in FIGS. 1 and 2. The interface is implemented using an instruction set stored in host computer 24 (FIG. 2) and displayed on the host computer monitor. At the scan user interface, an operator selects the scan mode, i.e, helical or axial, as well as the various scan parameter associated with each mode. The selections are made, for example, by the user simply touching the desired area corresponding to the desired parameters. Touch sensitive interfaces are well known. Of course, many other types of interfaces could be used, and the interface illustrated in FIG. 3 is only an exemplary interface.

In the helical mode, the operator selects the desired slice thickness, the scan mode, and the scan speed. The "Hi-Q" scan corresponds to a high image quality scan and the "Hi-Speed" scan corresponds to a fast patient table speed, as described above in connection with Table 2. In the axial scan, the operator selects the desired slice thickness and the number of images to be generated per rotation.

Before now, no multi-slice CT system provides the scalable scan management, control, and image reconstruction processes, and scalable image display and analysis, as provided with the present system. With the present system, an operator can readily and simply select the desired number of slices and the slice thickness for images to be displayed. In addition, increased patient scan speed, improved image quality, and reduced x-ray tube loading are achieved.

Figure 4:
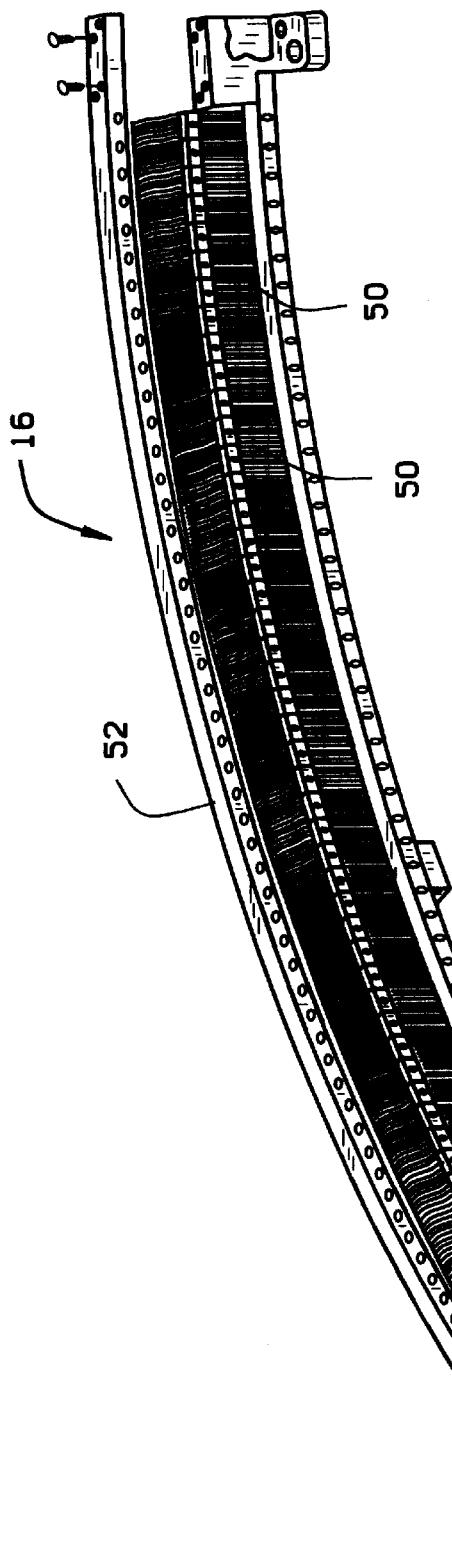
FIG. 4 is a perspective view of a CT system detector array.
Figure 5:
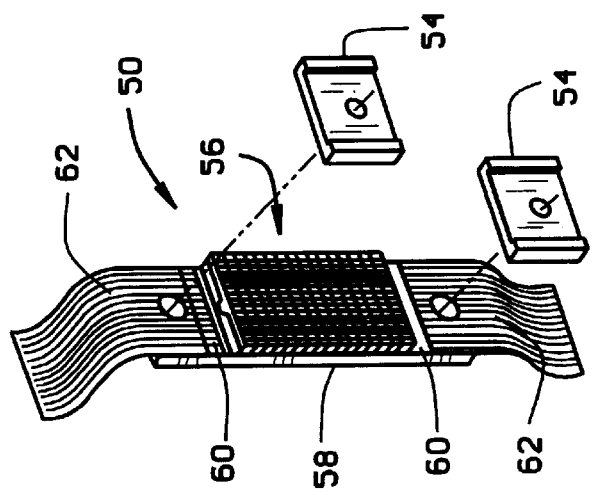
FIG. 5 is a perspective view of a detector module shown in FIG. 4.

With respect to one specific detector configuration, and referring to FIGS. 4 and 5, detector 16 includes a plurality of detector modules 50. Each detector module 50 is secured to a detector housing 52 by plates 54. Each module 50 includes a multidimensional scintillator array 56 and a high density semiconductor array (not visible). A post patient collimator (not shown) is positioned over and adjacent scintillator array 56 to collimate x-ray beams before such beams impinge upon scintillator array 56. Scintillator array 56 includes a plurality of scintillation elements arranged in array, and the semiconductor array includes a plurality of photodiodes arranged in an identical array. The photodiodes are deposited, or formed on a substrate 58, and scintillator array 56 is positioned over and secured to substrate 58.

Switch and decoder apparatus 60 are coupled to the photodiode array. The photodiodes are optically coupled to scintillator array 56 and have electrical output lines for transmitting signals representative of the light output by scintillator array 56. Particularly, each photodiode produces a separate low level analog output signal that is a measurement of the beam attenuation for a specific scintillator of scintillator array 56. The photodiode output lines extend from opposing sides of the semiconductor, or photodiode, array and are connected (e.g., wire bonded) to respective apparatus 60.

Switch apparatus 60 is a multidimensional semiconductor switch array of similar size as the photodiode array, and switch apparatus 60 is coupled in electric circuit between the semiconductor array and SDAS 42 (FIG. 2). Apparatus 60, in one embodiment, includes a plurality of field effect transistors (FETs) arranged as a multidimensional array. Each FET includes an input line electrically connected to one of the respective photodiode output lines, an output line, and a control line (not shown). FET output and control lines are electrically connected to SDAS 42 via a flexible electrical cable 62. Particularly, about one-half of photodiode output lines are electrically connected to each FET input line one side of the array with the other one-half of photodiode output lines electrically connected to the FET input lines on the other side of the array.

The decoder controls the operation of the FETs to enable, disable, or combine photodiode outputs in accordance with a desired number of slices and slice resolutions for each slice. The decoder, in one embodiment, is a decoder chip or a FET controller as known in the art, and the decoder includes a plurality of output and control lines coupled to the FETs and SDAS 42. Particularly, the decoder outputs are electrically connected to the switch apparatus control lines to enable the FETs to transmit the proper data. The decoder control lines are electrically connected to the FET control lines and determine which of the outputs will be enabled. Utilizing the decoder, specific FETs are enabled, disabled, or have their outputs combined so that specific photodiode outputs are electrically connected to SDAS 42. Further details regarding detector 16 are set forth in copending U.S. patent application Ser. No. (15-CT-4631), Photodiode Array For A Scalable Multislice Scanning Computed Tomography System, which is assigned to the present assignee and hereby incorporated herein, in its entirety, by reference.

In one specific embodiment, detector 16 includes fifty-seven detector modules 50. The semiconductor array and scintillator array 56 each have an array size of 16×16. As a result, detector 16 has 16 rows and 912 columns (16×57 modules), which enables 16 simultaneous slices of data to be collected with each rotation of gantry 12. Of course, the present invention is not limited to any specific array size, and it is contemplated that the array can be larger or smaller depending upon the specific operator needs. Also, detector 16 may be operated in many different slice thickness and number modes, e.g., one, two, and four slice modes. For example, the FETs can be configured in the four slice mode so that data is collected for four slices from one or more rows of the photodiode array. Depending upon the specific configuration of the FETs as defined by decoder control lines, various combinations of photodiode outputs can be enabled, disabled, or combined so that the slice thickness may, for example, be 1.25 mm, 2.5 mm, 3.75 mm, or 5 mm. Additional examples include, a single slice mode including one slice with slices ranging from 1.25 mm thick to 20 mm thick, and a two slice mode including two slices with slices ranging from 1.25 mm thick to 10 mm thick. Of course, many other modes are possible.

Figure 6:
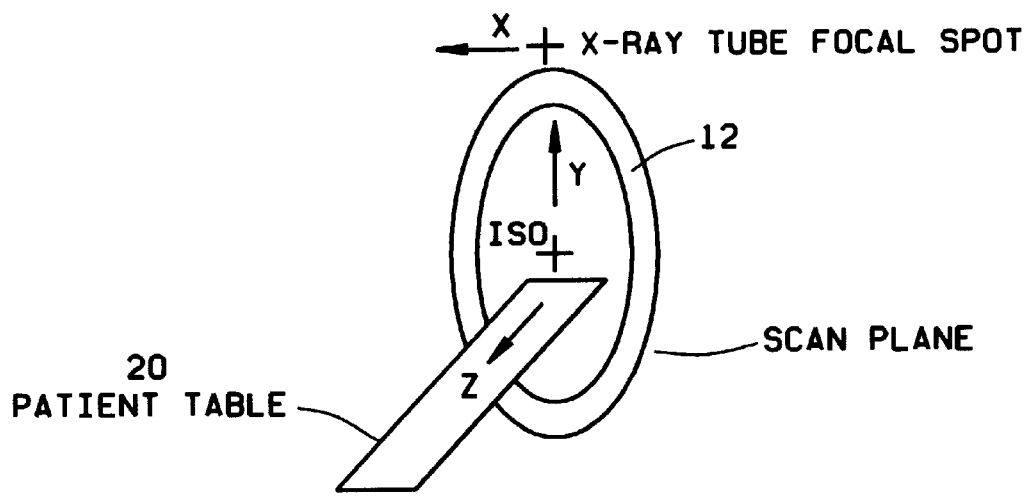
FIG. 6 illustrates the geometric configuration of the CT system illustrated in FIG. 1.

FIG. 6 illustrates the geometric configuration of the CT system illustrated in FIG. 1 and shows the gantry coordinate system. The coordinate system is referred to in the following figures. Particularly, the x-axis refers to an axis tangent to the circle of rotation of gantry 12. The y-axis refers to a radial axis extending from the iso center (ISO) of gantry 12 toward the x-ray tube focal spot. The z-axis is a longitudinal axis (in/out) with respect tot he scan plan. The patient is translated along the z-axis on patient table 20 during scanning.

Figure 7:
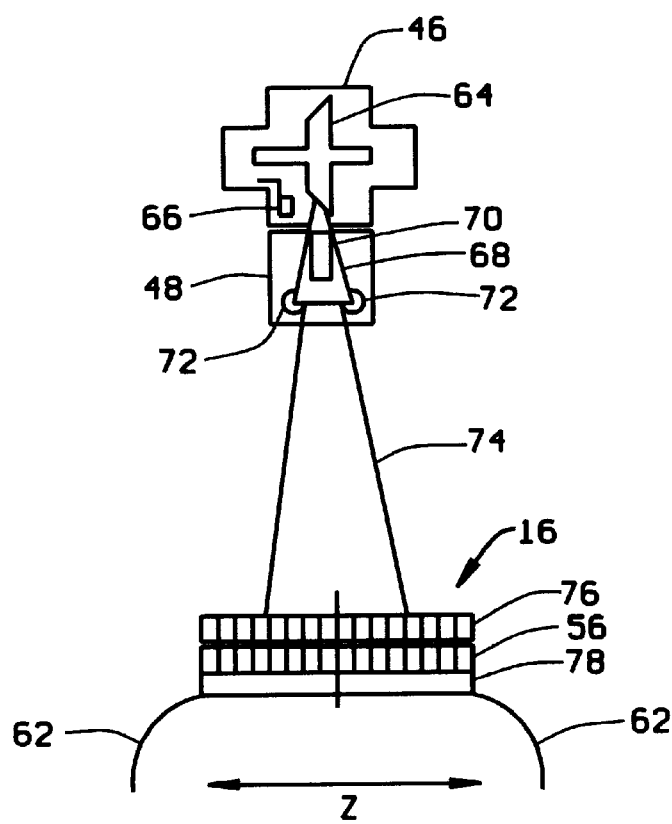
FIG. 7 is a schematic illustration of x-ray generation and detector components viewed from a side of the gantry.

Referring now to FIG. 7, and in multislice scanning, data is collected at various z-axis locations. Particularly, FIG. 7 is a schematic illustration of system 10 viewed from a side of the gantry 12. X-ray tube 46 includes an anode/target 64 and a cathode 66. An uncollimated x-ray beam 68 is emitted by tube 46 and passes through cam collimator 48. Collimator 48 includes a bowtie filter 70 and tungsten cams 72. Additional details regarding filter 70 are set forth in copending U.S. patent application Ser. No. (15-CT-4762), which is assigned to the present assignee and hereby incorporated herein, in its entirety, by reference.

As explained in connection with FIG. 2, the position of cams 72 is controlled by an on-board controller 40 which receives its commands from host computer 24 via SRU 32 and stationary controller 34. Stepper motors, for example, are connected to cams 72 for precisely controlling the position of cams 72. Cams 72 of cam collimator 48 can be independently adjusted with respect to the spacing between cams 72 and their location relative to the center of the collimator opening depending on the user selected data collection mode.

A collimated x-ray beam 74 is emitted from cam collimator 48, and beam 74 passes through patient 18 (FIG. 1)

and impinges upon detector 16. As described above, detector 16 includes a collimator 76, a scintillator array 56, and a photodiode/switching array 78 (the photodiode and switching arrays are shown as one unit in FIG. 7 but may be separate arrays as described above). Outputs from array 78 are supplied, via a flex cable, to SDAS 42 for processing.

The following description relates to operation of cam collimator 48 and detector 16 for providing scalability in the number of slices and the slice thickness. Although the operation of cam collimator 48 and the operation of detector 16 are sometimes described separately herein, it should be understood that collimator 48 and detector 16 operate in combination to provide the desired number of slices and slice thickness.

Figure 8A:
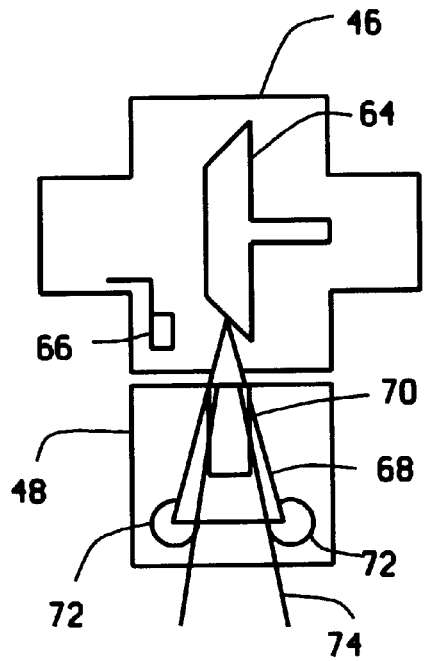
FIGS. 8A, 8B, and 8C illustrate operation of the cam collimator in the CT system illustrated in FIG. 1.
Figure 8B:
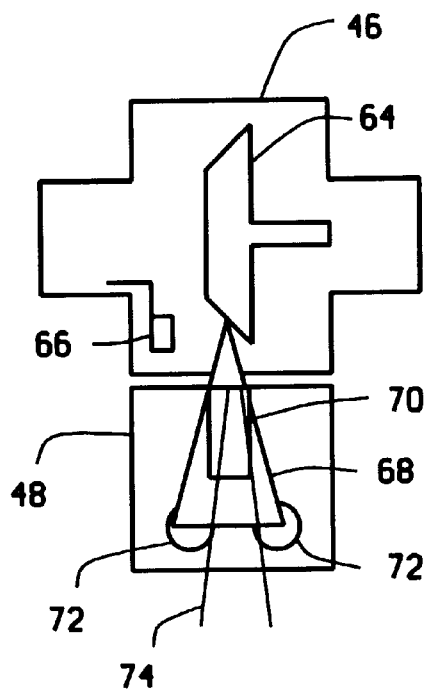
Figure 8C:
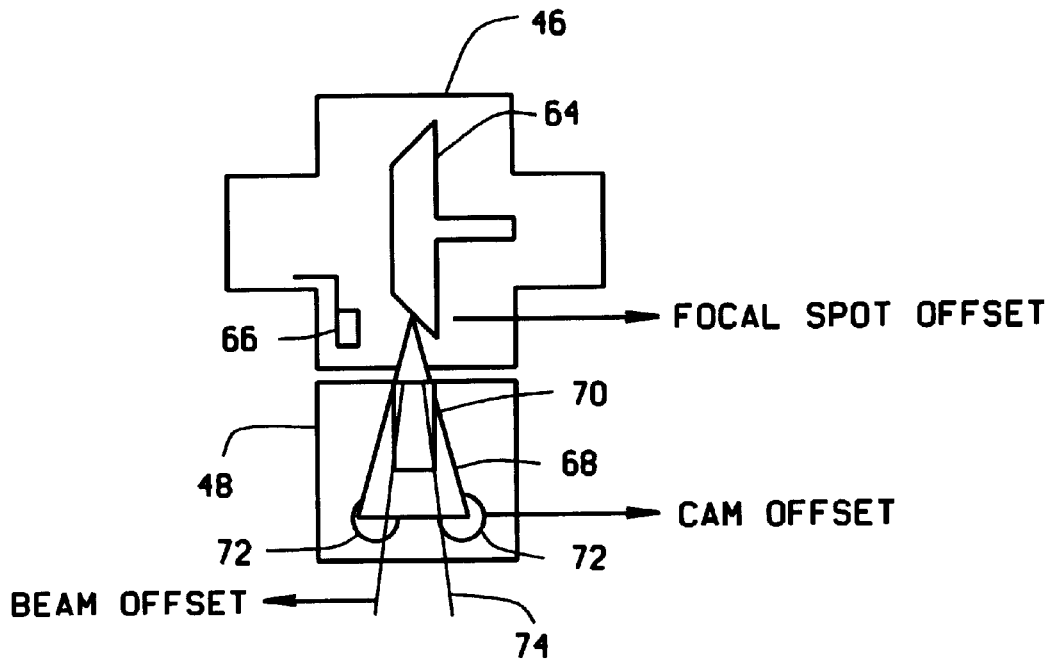

More specifically, FIGS. 8A, 8B, and 8C illustrate operation of cam collimator 48. FIG. 8A illustrates cam collimator 48 configured to emit a centered wide beam (e.g., a beam for obtaining 4 slices of data with a 5 mm slice thickness). For a narrow centered beam, and as shown in FIG. 8B, cams 72 are moved inward an equal amount relative to a center of beam 68. For example, the cam collimator configured shown in FIG. 8B could be used for obtaining 4 slices of data with a 1.25 mm slice thickness.

Collimator 48 also can be used to adjust for z-axis beam offset which may occur during operation of tube 46. Particularly, and referring to FIG. 8C, cams 72 can be positioned at unequal distances from the center of beam 68, as indicated by the arrow associated with the legend "cam offset". By offsetting cams 72 as shown in FIG. 8C, beam 74 is offset as indicated by the arrow associated with the legend "beam offset".

As described below in more detail, by controlling the position and width of beam 74 at cam collimator 48, scans can be performed to obtain data for many different slice numbers and slice thicknesses. For example, FIG. 9A corresponds to a selected detector configuration when it is desired to obtain 4 slices of data with a slice thickness of 5.0 mm. Cams 72 are separated wide apart in the z-axis direction to provide 20 mm collimation, and the photodiode outputs are combined by switching array 78 into four separate slices. Particularly, each slice of data combines the outputs of four photodiodes into one signal (1A, 2A, 1B, and 2B), and each slice data signal (1A, 2A, 1B, and 2B) is supplied to SDAS 42 via flex cables 62.

Figure 9A:
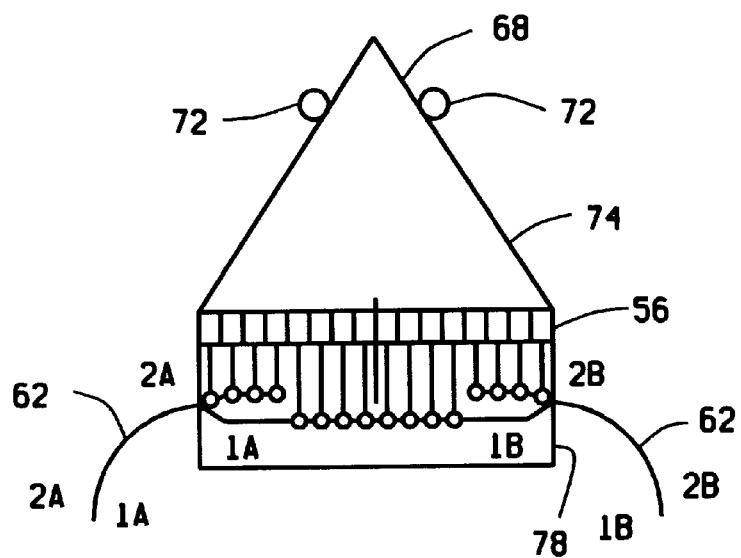
FIGS. 9A, 9B, and 9C schematically illustrate collection of scan data for various number of slices and slice thicknesses.
Figure 9B:
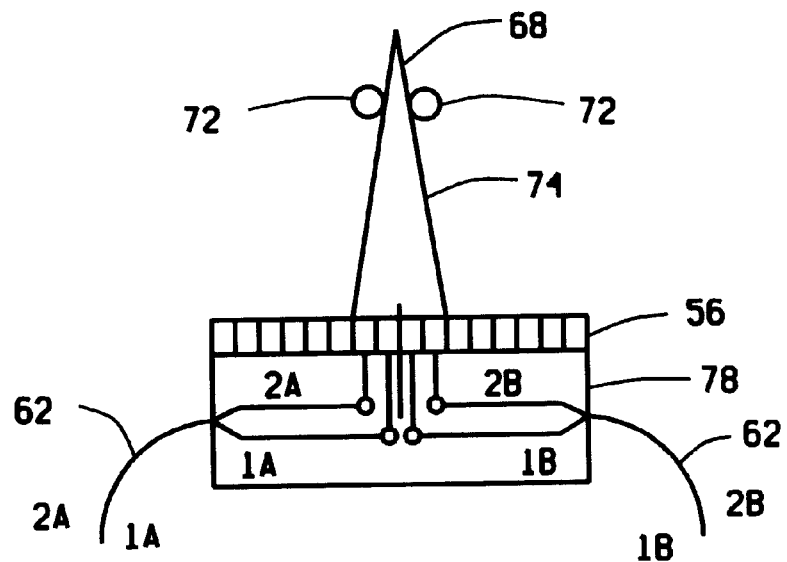

For four slices of data with a 1.25 mm slice thickness, the detector configuration shown in FIG. 8B may be utilized. Particularly, cams 72 are not separated as wide apart as for the 5.0 mm slice thickness (FIG. 9A). Rather, cams 72 are separated in the z-axis direction to provide 5 mm collimation, and the photodiode outputs are combined by switching array 78 into four separate slices. Particularly, each slice of data combines the outputs of one photodiodes into one signal (1A, 2A, 1B, and 2B), and each slice data signal (1A, 2A, 1B, and 2B) is supplied to SDAS 42 via flex cables 62.

Figure 9C:
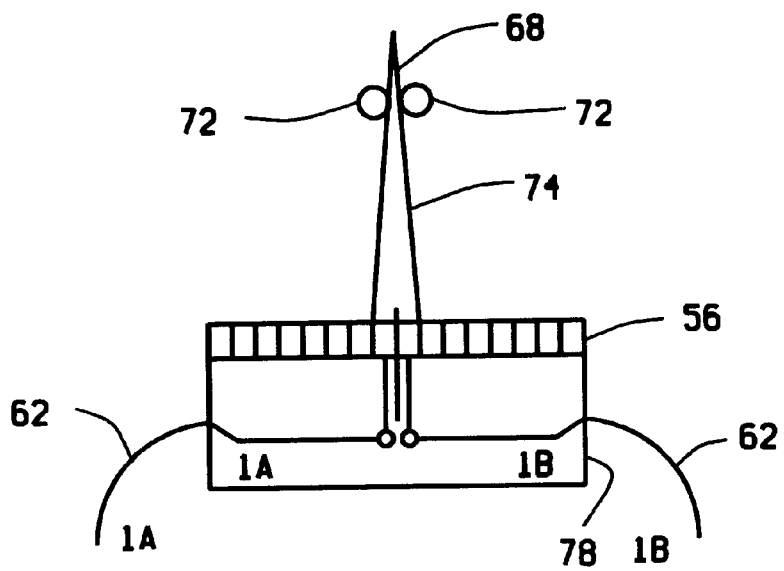

Of course, many other combinations of slice number and slice thickness are possible using system 10. For example, and referring to FIG. 9C, for two slices of data with a 1.25 mm slice thickness, cams 72 are separated in the z-axis direction to provide 2.5 mm collimation. The photodiode outputs are combined by switching array 78 into two separate slices. Particularly, each slice of data combines the outputs of one photodiode into one signal (1A and 1B), and each slice data signal (1A and 1B) is supplied to SDAS 42 via flex cables 62. By controlling cam collimator 48 and channel summation along the z-axis as described above, scan data can be collected for many different slice numbers and slice thicknesses.

Figure 10A:
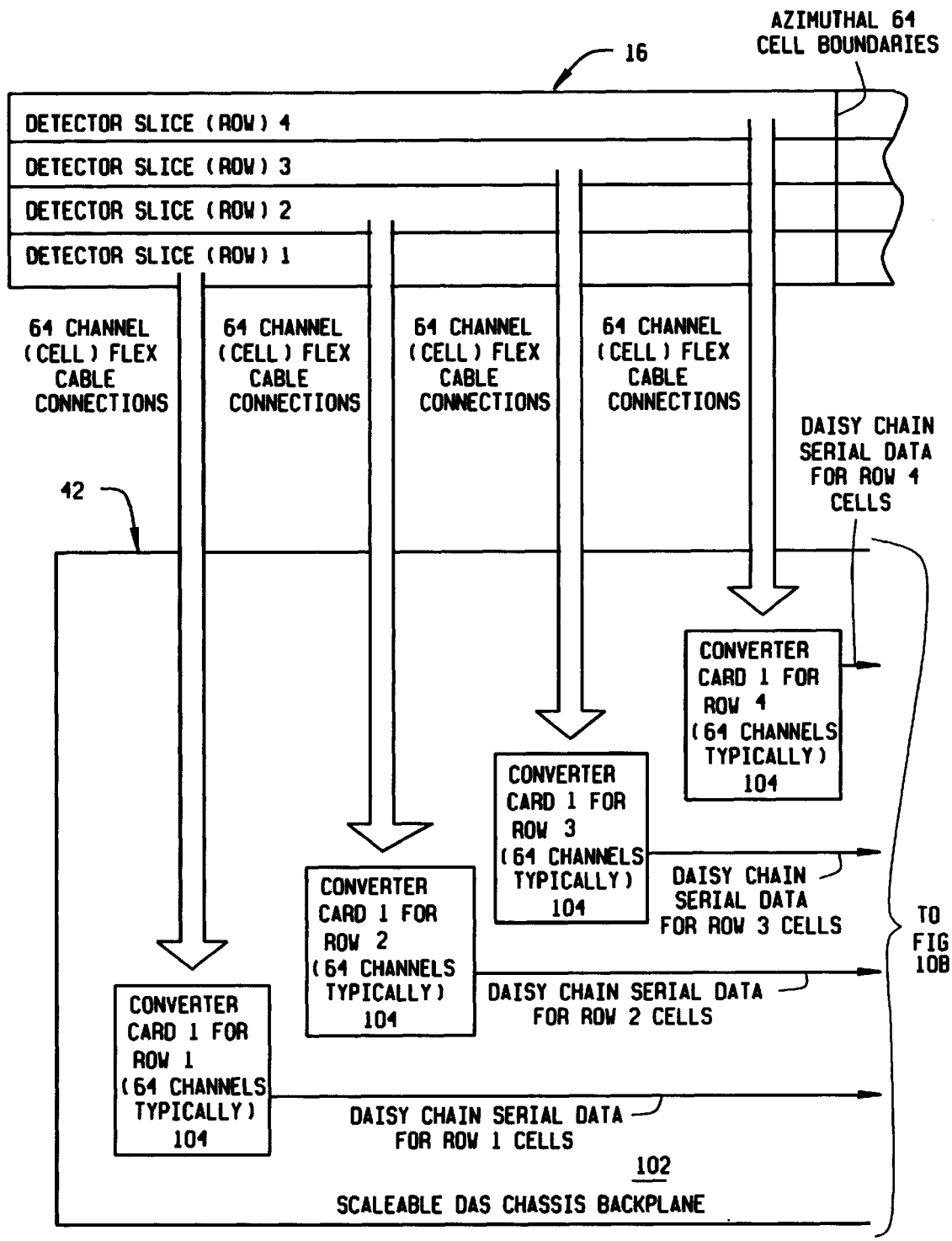
FIGS. 10A, 10B, and 10C together form a component block diagram illustration of the scalable data acquisition system coupled to the detector.
Figure 10B:
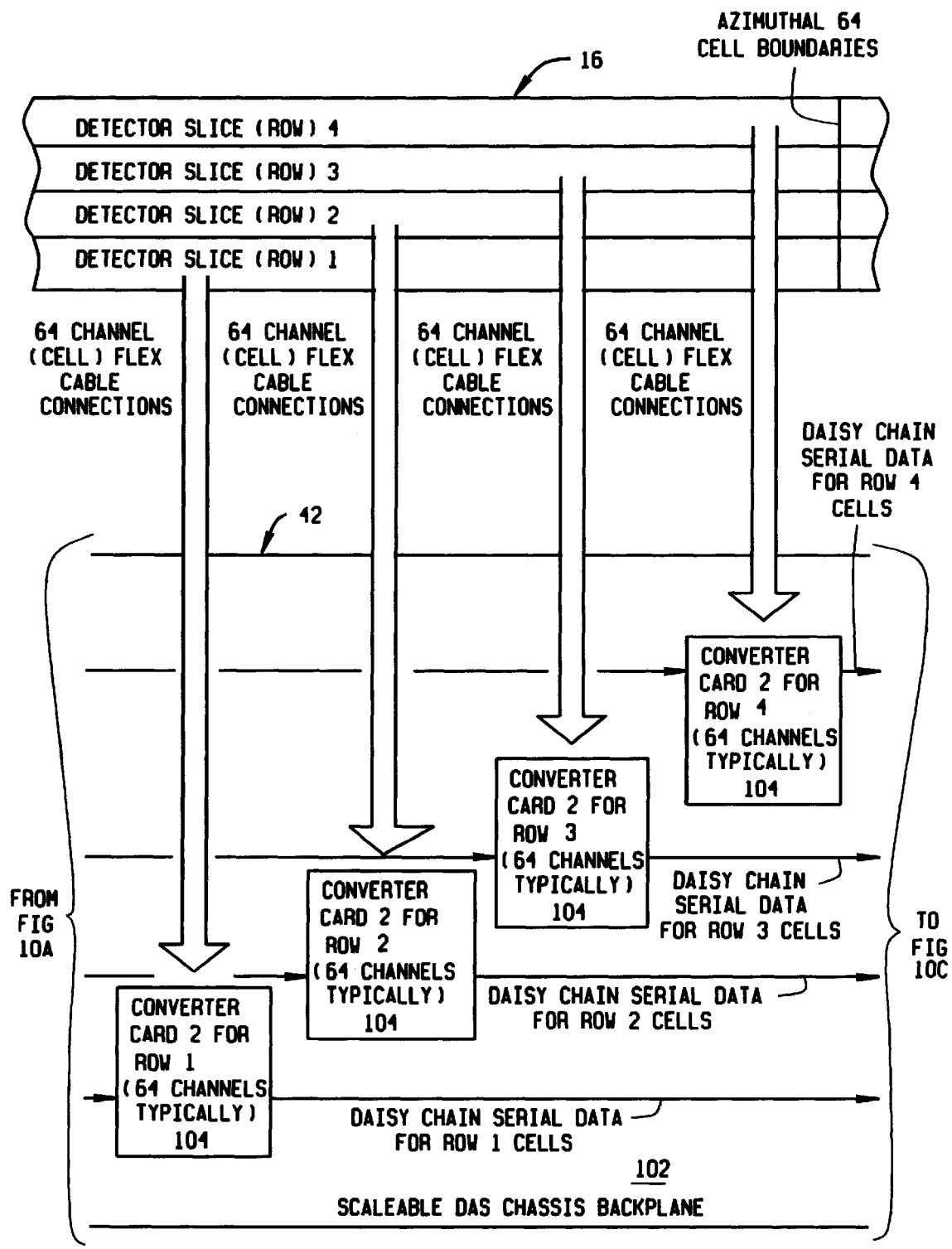
Figure 10C:
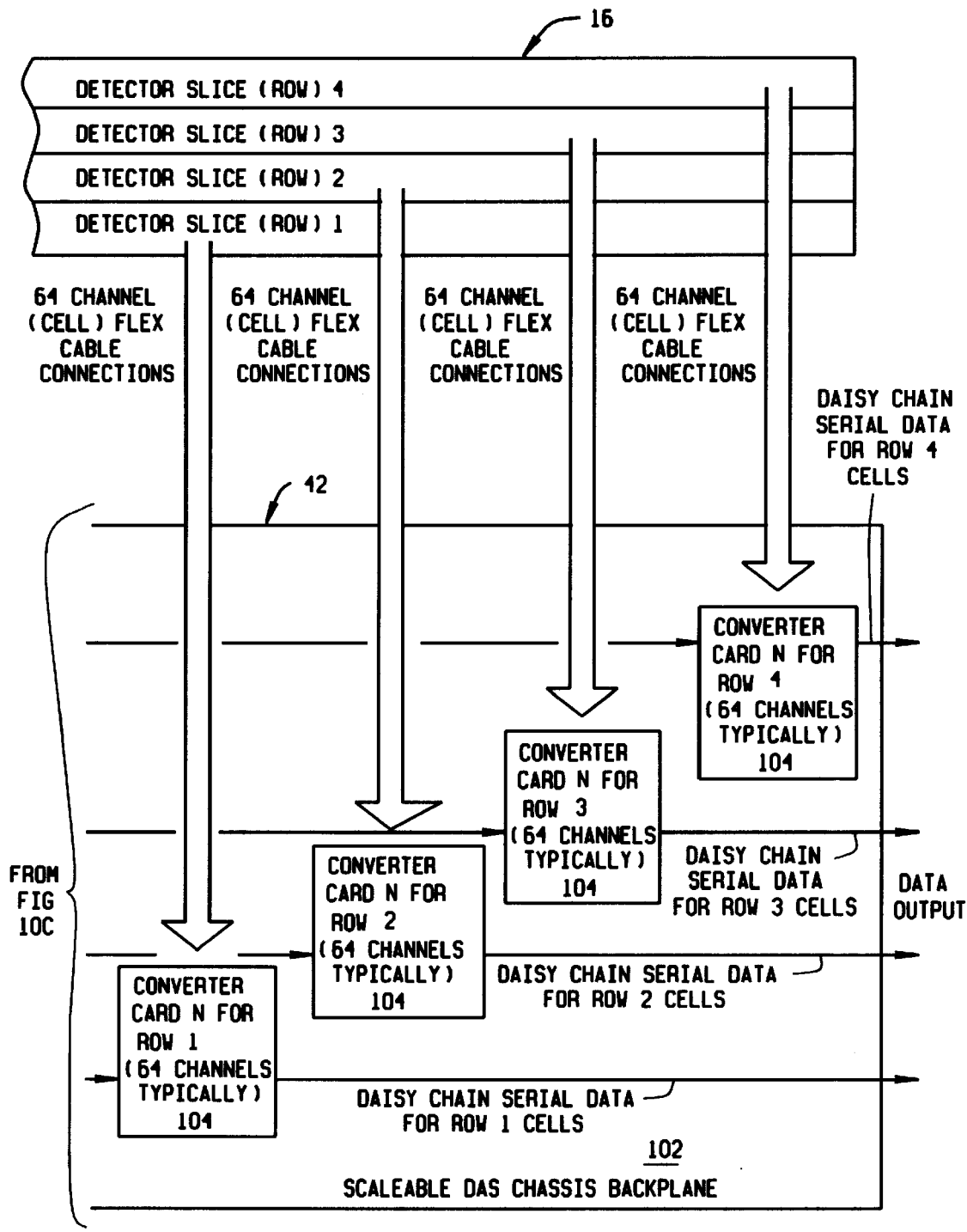

FIGS. 10A, 10B and 10C together form a block diagram of a scalable data acquisition system (SDAS) 42 which is easily reconfigured to be used with either single slice or multi-slice detector systems. SDAS 42 can be reconfigured by adding or removing printed circuit boards to accommodate the number of slices provided by detector 16.

As explained above, SDAS 42 converts the low level electrical current signal from x-ray detector 16 to digital values for image reconstruction, display and archive. Single slice third generation, fan-beam CT systems typically contain 300 to 1000 cells in the azimuthal direction. SDAS 42 correspondingly is required to provide an anti-alias filter for each cell prior to Analog to Digital Conversion (ADC). SDAS cells are typically referred to as channels. Detector cells can be ganged or paralleled to one SDAS channel as described above. The ganging reduces spatial resolution. On the outer edges of the fan beam this resolution loss is not an application limitation and allows the production of detector cells of the same size throughout detector 16. An advantage of ganging is a reduction in the number of required SDAS channels and the associated cost. The digital output from SDAS 42 is usually transmitted either in a serial or semi-serial fashion, as described below in more detail, to reduce the amount of interconnecting hardware.

Analog current signals from detector 16 are connected to the SDAS input channels via shielded ribbon or flex cables. The cables are connected to SDAS 42 at the DAS backplane 102. DAS Converter boards 104 are also plugged into DAS backplane 102. This interconnection provides several advantages. For example, backplane 102 enables ganging the detector cells on the outside edges of the fan beam. Backplane 102 also allows a redistribution of the detector cells to appropriate converter boards 104. Signals from more than one slice are contained in the same flex cable. Each converter board 104 only serves one slice since the reconfiguration of SDAS 42 from one multi-slice configuration to another or to the single slice configuration requires only the removal or addition of converter boards 104. Also, backplane 102 enables a blending or weaving of SDAS channels and detector cells near the end channels of a converter board 104. Artifacts such as a band in the image are usually the result of common or uniform error source across one group of adjacent channels versus a neighboring group of channels. If all the channels on one converter board 104 have a common error difference compared to a neighboring converter board 104, this type of image artifact is quite likely. By interweaving detector cell assignments versus converter card 104 on the edges of converter card 104, the susceptibility to a band artifact is reduced.

Another aspect of the SDAS 42 is that converter cards 104 which combine the anti-alias filter and ADC on the same board 104 rather on separate boards. Having the filter and ADC on the same board 104 enables the modularity required for scalable DAS 42. The integrated filter-ADC function on the same board 104 also limits the possibility of electromagnetic and conducted interference because of short electrical lead lengths.

Yet another aspect of SDAS 42 is the use of serial data transmission between converter boards 104 dedicated to a particular slice. Adding more slices thus simply adds more serial data streams. SDAS 42 uses a daisy-chain serial bus, but a broadcast bus could be used. The advantage of the daisy-chain bus is the shortness of lead lengths for the transmitted signals. Short lead length enables use of less robust and expensive drivers. The daisy chain bus is a buffering and retransmission of the received data, with the data from the receiving board being inserted in-time in front of the received data. The daisy-chain bus is similar to a long serial shift register running the length of the SDAS chassis, with each converter board 104 providing one section of the shift register.

Figure 11:
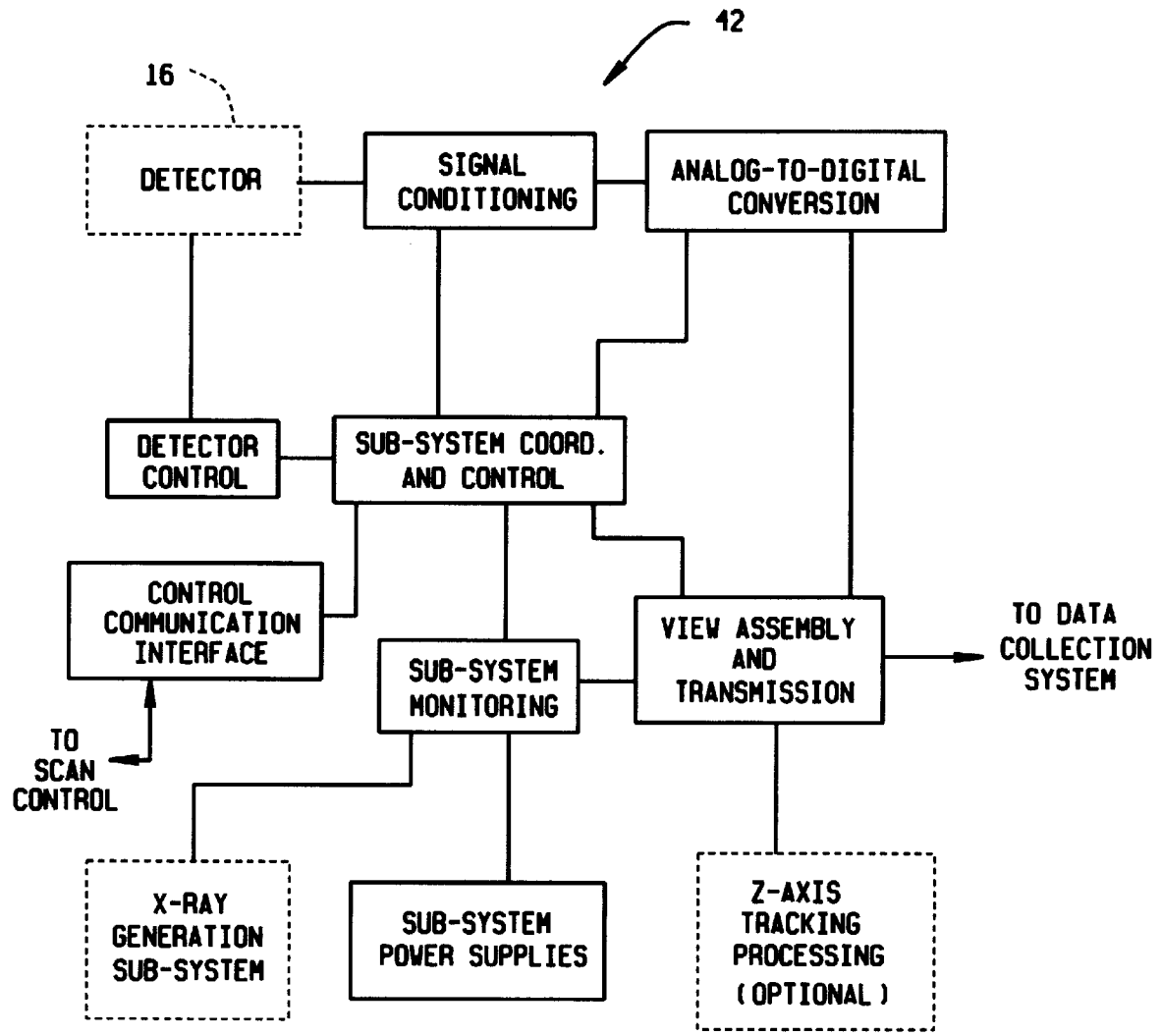
FIG. 11 is a functional block diagram of the scalable data acquisition system.
Figure 12A:
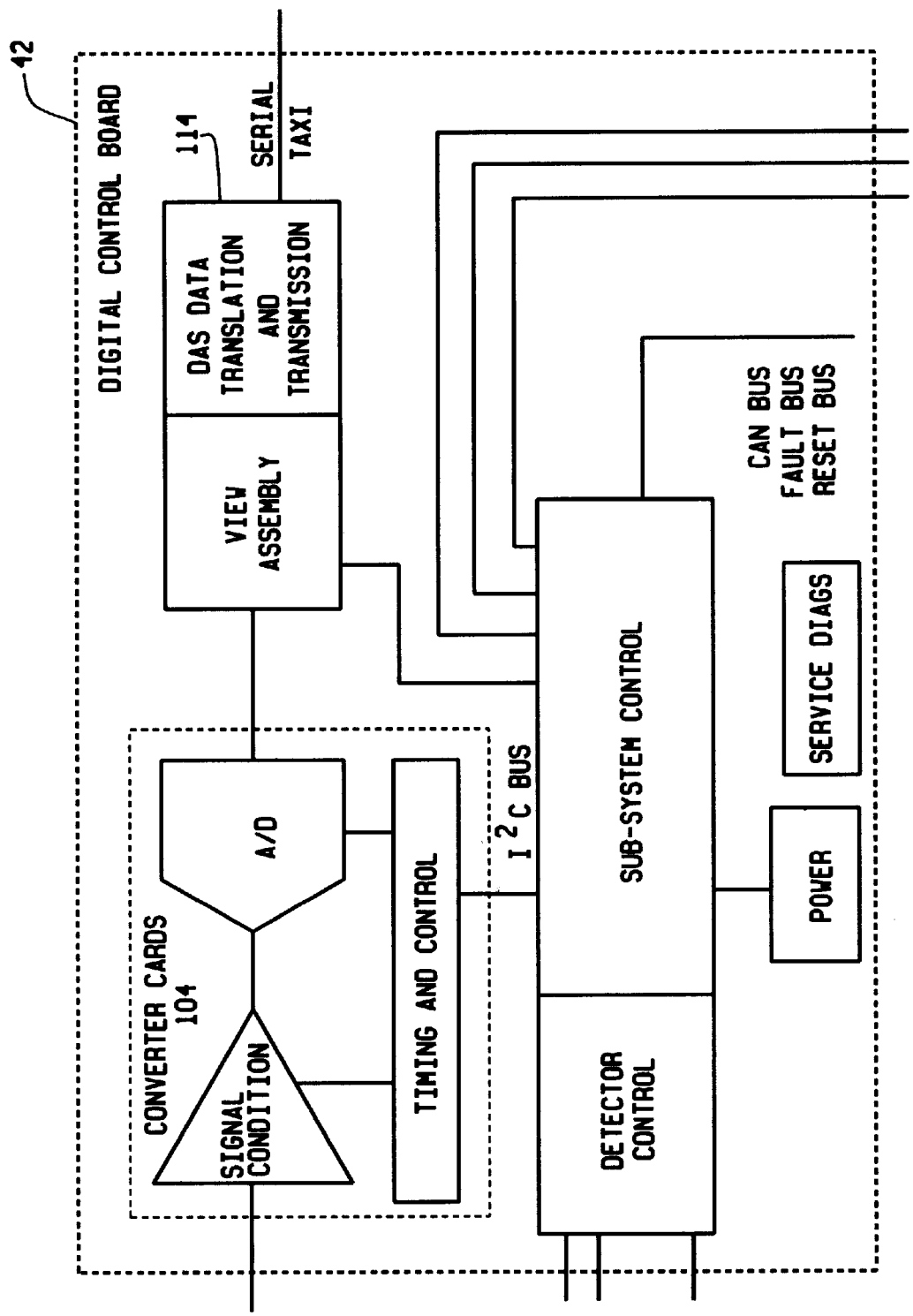
FIGS. 12A and 12B together form a schematic block diagram of the SDAS coupled to other components of the multislice imaging system.
Figure 12B:
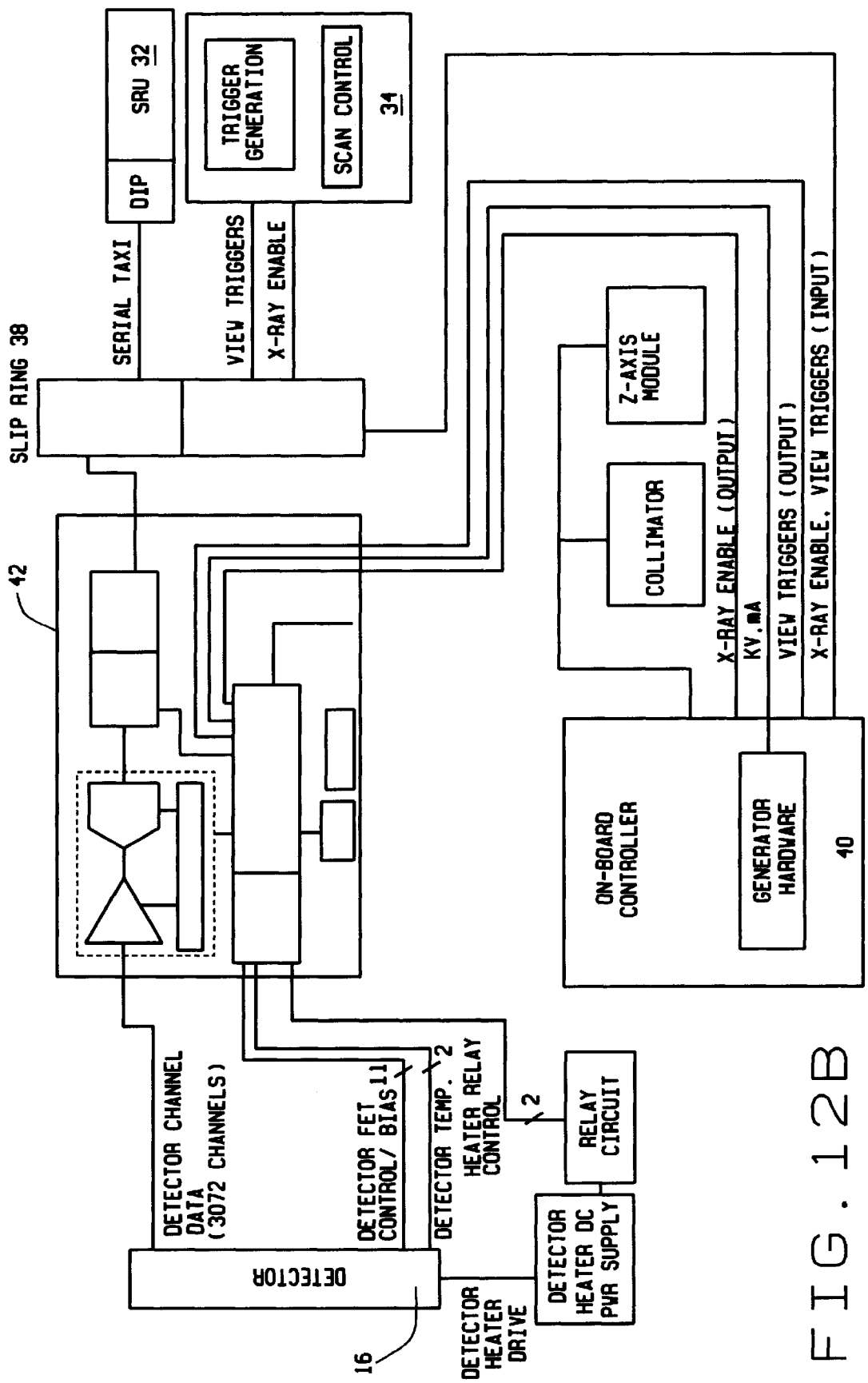

FIG. 11 is a functional block diagram of SDAS 42, and FIGS. 12A and 12B together form a schematic block diagram of SDAS 42 coupled to slip ring 38 and detector 16. As explained above, SDAS 42 processes low level analog signals from detector into digital data. Once in digital form, the signal is manipulated and transmitted to the scan data processing subsystem for storage to the disk drive. Z-axis data is extracted from this data stream to provide feedback for the X-ray beam aiming mechanism.

Referring now specifically to FIGS. 11, 12A, and 12B, one embodiment of SDAS 42 is illustrated. More specifically, converter cards 104, low level analog electrical current signals are converted to analog voltage signals. Each signal conditioning channel includes a selectable multi-gain "boxcar" integrating amplifier and a sample/hold function, and supports output channel multiplexing. The sample/hold function provides simultaneous sampling of the channels. Excluding the auxiliary channels, the signal conditioning has up to 3072 separate channels.

Several signal adjustments may be made via control registers contained on each converter card 104. Each of these register is accessed via the 12C bus from the digital control board (DCB), and ultimately the microcontroller on each of the converter boards. Pre-amplifier application specific integrated circuits (ASICs) contain a control register to trim the offset voltage presented by the converter card 104 to the detector. The microcontroller on the converter card 104 sets or loads the registers via a single 8 bit wide serial port register. One bit of the pre-amp serial port is dedicated to each of the 8 different pre-amplifier ASICs on the converter card 104. Every time the microcontroller does a write to the pre-amp serial port register, the data in the 40 bit serial register in the individual pre-amplifier is serially shifted by one bit. Five different bits are required to control each of the eight channels or integrators contained within a pre-amp ASIC. Thus, forty total bits or writes are needed to completely set or change the offset trim parameter for each channel. Further since there or eight pre-amp ASICs per converter card 104, 320 bits must be written.

The FFP data values from the converter board, and ultimately the DAS itself, are unipolar in nature. However, with no input signal from detector 16, or very little input signal from detector 16, the channel output can just as likely have a negative offset as a positive offset. A relatively small constant positive value is added digitally to the channel readings before the readings are transmitted out of the converter boards, to ensure all values are positive with zero input. This value is setable with a single eight bit value or register. The value is a straight binary number whose least significant bit is equal to 32 DAS counts (128 Converter Board counts).

Converter cards, or boards, 104 implement a two stage signal conversion process on the outputs from each of the 64 pre-amplifiers or channels. The first stage is an autoranging programmable gain amplifier, or often commonly referred to as a Floating Point Amplifier (FPA). The FPA is used to determine the exponent bits in the output data words, as well as correspondingly gain the analog signal before conversion by the second stage, a binary Analog to Digital (A/D) converter.

Because the FPA offset is inherently different for each of the four (4) different FPA gains, an FPA Autozero function is implemented on converter boards 104. This function provides seamless or transparent operation to the rest of the system when the FPA gain is automatically changed as a function of signal level.

Several diagnostic modes or features may be implemented as part of the FPA Autozero function. The FPA Autozero function can be disabled. The DCB can be operated in a diagnostic mode to read the FPA offset conversion values in lieu of 8 of the 64 normal data channels, which permits checking externally if the Autozero average value is being correctly calculated and permits verifying that the FPA offsets are within a normal or expected range going into the FPA Autozero correction function. Firmware sets all converter board pre-amplifier gains to the value specified in the scan Rx. All pre-amplifiers on all converter boards 104 are set to the same gain. In addition, firmware places the integrators, which are used to accumulate detector output, into standby mode so that the integrators will not saturate. Saturation results in application of a bias voltage to the detector and may cause lengthy full recovery times. Pre-amp standby is done any time triggers have not been received for some time nor are expected to be received for some time (e.g., 0.5 sec).

Firmware also sets the input offset voltage offset trim values. A calibration algorithm may be used to determine the correct values to download at power-up. The calibration only needs to be done on vary rare occasions, for example, when converter cards 104 are repaired or replaced. Otherwise the offsets should be stable. Final input offset calibration is done after SDAS 42 has had a chance to temperature stabilize. Firmware sets the channel output bias value.

For diagnostic purposes, firmware enables and sets a special analog test voltage into the signal conditioning stage of the converter boards. The test voltage is programmable in 16384 steps between 0 and −3 volts. It is used in the diagnosis of the SDAS acquisition and signal processing chain. The analog test signal can be enabled to either the input of the pre-amplifiers, or to a special test input channel on the analog mux in the FPA. The firmware also sets a 1 to 16 multiplication factor with respect to the test voltage when it is enabled into the pre-amplifier stage.

The automatic corrections can be disabled, and therefore, offset trim corrections, channel output bias, and autozero corrections can be disabled. Channel output bias is turned off by loading the channel output bias register with a value of zero. Input voltage offset trim is turned off by downloading a value equal to zero trim (inherent offset) to the pre-amp ASIC serial offset trim register.

Firmware may also place the channel sequencing in several diagnostic modes, i.e. single channel, repeat same channel four times, and sequence between grounded input to the FPA and a normal channel. The diagnostic channel sequencing modes are useful in troubleshooting problems on the converter boards.

The Analog to Digital (A/D) converters convert each of the following analog voltages to a digital word linearly proportional to the input signal level. The outputs are read once per view trigger and sent to SRU 32. To increase the dynamic range of the A/D converters, an autoranging floating-point amplifier scales the signal to appropriate levels and provides a two bit exponent to represent the scale factor used.

| Description | Convert A/D | DCB A/D |
| --- | --- | --- |
| Exponent | 2 Bits | NO |
| Mantissa | 14 Bits | 16 Bits |
| Inputs Measured | All Detector Signal Outputs | All SDAS Power Supplies, Analog Test Voltage kV, mA, and Detect. Heater Temperature |
| Refresh Rate | Once Per View Trigger | 1408 Hz minimum |

Firmware is not utilized for the actual conversion process. Once per scan (patient), an A/D calibration cycle for each converter board and DCB is performed to ensure optimum performance at the then SDAS temperature. Firmware places the autoranging FPA in any of the 8 different fixed gain diagnostic modes. Firmware also is utilized to configure the converter board A/D so that it will send "canned" data which will include data identifying the converter card number, and channel being sent.

In the embodiment shown in FIGS. 11, 12A, and 12B, there is no Z-Axis tracking performed by SDAS 42. However, SDAS 42 provides support for external Z-axis processing by making all Z-axis data available over the digital auxiliary data interface (DADI). An optional Z-Axis Module (ZAM) can be connected to SDAS 42 through this interface to perform real-time Z-Axis processing. SDAS 42 supplies the required data on a view to view basis to the ZAM. After sending these data, SDAS 42 allows a 782 us window for the ZAM to process the information and return the results. There is no requirement on when the ZAM can start returning results. The only requirement by SDAS 42 is to have all results returned within the allowed time window. The returned Z-Axis tracking data is included in the view data stream. If no data are returned within the time window, then the previously received Z-Axis tracking data or the power-up values are included to the view data stream instead. This ensures safe SDAS operations with or without a ZAM.

The view assembly function is performed to collect all data needed to assemble a view and transmit it to the scan data processing subsystem, and also to extract the necessary data from the view data stream to support diagnostics and Z-axis processing. SDAS 42 generates internal view triggers when external triggers are not desired or present. The period of such triggers is defined by a register count:

Internal Trigger Period=16 Bit Register Count×Shift Clock (26.8 MHz) Period

Both external and internal triggers signal SDAS 42 to perform the same operations as described below. When internal triggers are enabled, SDAS 42 ignores any external trigger. The number of internal triggers generated is monitored and controlled by firmware.

Premature Trigger Detect

SDAS 42 reports an error condition if a trigger is received before it is enabled and ready for view collection.

Trigger Jitter Detect

SDAS 42 monitors the period between consecutive triggers. When this period falls outside the acceptable tolerance according to the scan speed, SDAS 42 reports an error condition.

View Collection

SDAS 42 begins view collection and transmission every time a valid trigger is received.

Trigger Timeout Detect

SDAS 42 ends view collection normally in Scan or Offset mode when a trigger timeout is detected. The timeout period is two times the trigger period for that scan speed.

Trigger Duration Error Detect

SDAS 42 monitors the duration of each trigger to prevent a trigger stuck or inverted condition. When this duration falls outside the acceptable tolerance, SDAS 42 reports an error condition.

Converter Data Collection

SDAS 42 receives serial digital data streams from the A/D Converters for each detector row. A serial to parallel conversion is done on these data first, followed by a parity check. In this specific embodiment, the raw data with parity is 19 bits long. In order to optimize storage space and view transmit size, SDAS 42 reduces each data to 16 bits by discarding all parity and 2 LSB'S.

Diagnostic View Select

Instead of real converter data, SDAS 42 is configured to inject one view worth of test data for diagnostic view generation. The diagnostic view can be offset or scan type and is be predefined by firmware. Once defined, the same test data can be used repeatedly from view to view without reloading.

In addition to data from the converter boards, SDAS 42 also takes a snap shot of other information at each view trigger as described below.

1) Scan Data Type. Either Offset or Scan data depending on the received Scan Rx.
2) kV and mA measured by the generator.
3) All power supply levels monitored by SDAS 42.
4) Starting View Angle—defined by scan control. View angle of the gantry at the point when the first SDAS trigger was generated.
5) View Sequence Number. Sequence number of the current view is reset to 1 before entering Scan/Offset data collection.
6) Zaxis Tracking Data returned by ZAM.
7) Data record format revision.
8) Data record view length in bytes.
9) Detector Heater Temperature SDAS 42 performs a checksum on all view data to preserve data integrity. The checksum is 32 bits long and is the result of adding all view data bytes together. In order to avoid any undetected data corruption by SDAS 42, the checksum is performed early in the stream after the serial to parallel conversion phase. SDAS 42 also is configured to repeatedly transmit the same diagnostic view data. This is accomplished using the SDAS internal triggering circuit and diagnostic input data.

After assembling all data for a view, SDAS 42 performs the following functions before transmitting the view data SRU 32. Transmission can be disabled by firmware via setting a bit in a register. Specifically, the order in which data can be collected by SDAS 42 is different from the transmit order expected by SRU 32. SDAS 42 therefore uses a lookup table to save the data in the desired order. Such a table is sometimes referred to as the Translation Table. Since most data are 16 bit wide, every entry in the Translation Table then becomes an address indexing to a 16-bit location in memory. The Translation Table is downloaded by firmware after power-up and can be changed for different backplane and/or converter board populations.

Also, SDAS 42 can transmit each 16 bit data, recalled by the Translation Table to SRU 32, in either Big or Little Endian format. Big Endian format sends the MSByte of the 16 bit data first and vice versa for Little Endian format. Format selection is done by setting a bit in a register. SDAS 42 also performs real time Forward Error Correction (FEC) encoding on all data bytes before transmissions to SRU 32.

Such FEC encoding is described in co-pending U.S. patent application Ser. No. (15-CT-4764), which is assigned to the present assignee and hereby incorporated herein, in its entirety, by reference. SDAS 42 saves the most recently sent data view in a buffer for verification and diagnostic purposes. Firmware can examine this buffer once data collection is disabled.

Each time SDAS 42 collects data, offset or view, it sets up a number of data header fields. Specifically, depending upon the type of data collected, offsets or scan data, firmware writes the appropriate view record type, i.e., the magic number, and record size into the Magic Number field. Firmware also "zeros" the View Sequence field before the collection of offset and scan data. When the value of the firmware view angle is known, firmware also writes the value of the first view angle into the View Angle field.

As data is acquired, firmware requires notification, via interrupt, of the following View Assembly and Transmission events.

Acquisition of the first view of data.
  Acquisition of the last view of data.
  Detection of a parity error.
  Detection of trigger jitter.

Since SDAS 42 is scalable, firmware configures, or controls, the following View Assembly and Transmission aspects Channel order in the output view data record.
  Data representation (order) in the output view data record. (i.e., Big or Little Endian data).
  Selective data stream enable and disable. For example, if SDAS 42 is populated with converter cards 104 sufficient for only two data streams, the unused data streams will be disabled so that no parity errors will be detected on those streams.

In order to perform diagnostics, the firmware controls the following View Assembly and Transmission aspects:

Data flow through the acquisition system.
  Ability to look at the data of a view after it has been acquired.
  Ability to disable data output. This is to prevent the data from confusing sub-systems down stream from SDAS 42 whenever SDAS 42 performs internal diagnostics.
  Ability to create a view of a known pattern and be able to send it at standard acquisition rates, using either internal or external trigger sources. This is referred to as simulated data mode. In this mode, the view header is updated as if the data were actually coming from the converter boards.
  Ability to create a single view, of known data, and to send it.

SDAS 42 generates 15 signals to configure the detector MUX circuitry. Each signal can either be "On" or "Off" according to its controlling register bit value. The power-up or default state is 'Off for all signals. Firmware configures these register bits appropriately prior to a scan. SDAS 42 also monitors the detector temperature continuously at the rate of 1408 Hz minimum. SDAS 42 automatically enables and disables the detector heater circuit according to the temperature set points stored in registers.

More particularly, upon receipt of a scan Rx, SDAS 42 configures the detector MUX circuitry for the correct number of macro rows and macro row thickness at ISO. Since it is possible that SDAS 42 will support a number of detector types, on each detector, the settings needed for macro row thickness and number of macro rows are governed by a configuration table. This enables SDAS 42 to accept Rx parameters that are ISO center relative.

An A/D converter is used to measure the following. The converter has 16 bits of resolution. The measurements are updated at 1408 Hz minimum.

kV and mA levels from the OBC/Generator
  All SDAS power supply levels
  Test analog voltage generated by a 12 bit DAC
  Detector temperature thermistor reading The A/D converter continuously gathers data and writes this data into the auxiliary channels area of the data header. The firmware also reads auxiliary data channels at any time. Approximately every 250 ms, the firmware polls the auxiliary channels that contain DAS power supply voltages and tests the voltages. If a supply is found to be outside of its margin, a warning message is logged into the error log.

Whenever a SDAS Rx message is received, the firmware polls the detector temperature and tests the temperature against the following limits:

If the detector temperature is over a first temperature, issue a warning message and allow scanning to continue.
  If the detector temperature is under a second temperature, issue a warning message and allow scanning to continue.

Sub-system Coordination and Control primarily controls operation of SDAS 42. The control contains a MC68332 microcontroller (MCU), 1 Meg of RAM, 1 Meg of FLASH memory, an RS-232 serial port, a background debug mode (BDM) port, a status LED port, and a CAN bus interface. A 16.000 Mhz clock is used for the SDAS implementation of the core controller so that it may be able to accurately measure time down to one millisecond.

Upon a powerup or hardware reset, the control executes selftests which test the MCU core, and the SDAS hardware components. MCU programming, sub-system configuration, and sub-system characterization may be modified in the field by downloading a new program or new configuration/characterization data. All downloads are through the Control Communication interface. When a new MCU program is downloaded, it is buffered and checked for errors before being programmed into FLASH memory. When the SDAS configuration or characterization data is downloaded, the data is buffered and checked for errors before being programmed into FLASH memory.

When a sub-system is powered up, the first firmware run is the core controller, or platform, firmware. Platform firmware performs rudimentary MCU initialization and core controller specific selftests. After executing core controller selftests, the platform firmware determines whether FLASH memory contains executable SDAS application code. If application code exists, platform firmware copies application code from FLASH memory to RAM and begins its execution.

At this point, application firmware takes control of the MCU and all SDAS hardware. When given control, the SDAS application firmware completes the initialization of SDAS 42. This includes the following tasks:

Complete MCU initialization so that the MCU is able to access SDAS hardware.
  Perform powerup/reset tests on SDAS hardware.
  Initialize SDAS hardware.
  Initialize SDAS control tasks.

Once the SDAS application firmware is up and running, it is able to accept and process events generated either by the reception of a command via the control communication interface, or by an interrupt generated by SDAS hardware.

Whenever SDAS 42 receives a command, it generates a specific response as set forth in Table 3. If SDAS 42 is unable to properly execute the command, SDAS 42 notifies the system and, when applicable, logs an error message. SDAS operation is controlled via the SDAS control communication interface.

TABLE 3

DAS Command Response

| Command Message | SDAS Action(s) | Command Response |
|---|---|---|
| DAS Rx (This message signals the beginning of a scan.) | Setup detector per Rx parameters. Setup converter board Preamplifier gain. Execute converter board A/D calibration Enable converter preamplifier autozero mode. Place converter board A/D's to standby. Test detector temperature to limits described in DRS section 7.6.2. Configure SDAS hardware for view data acquisition. | Positive acknowledgment when command is successfully completed. Negative acknowledgment when there is an outstanding DAS error or unacknowledged DAS reset condition. |
| Reset DAS | DAS resets as if power were cycled or the reset button had been depressed. | Positive acknowledgment when command before command is executed. |
| Acknowledge Reset | Indicates that the DAS may now process the full DAS command set. | Positive acknowledgment when command is successfully completed. |
| Go To Standby (This message signals that the scanner does not intend to scan for "awhile".) | SDAS TAXI output disabled. SDAS beings to perform background diagnostics. (Which may be preempted by the DAS Rx.) | Positive acknowledgment when command is successfully completed. Negative acknowledgment when there is an outstanding DAS error or unacknowledged DAS reset condition. |
| First View Angle | The number presented to the SDAS with this command is written, unaltered, into the appropriate view header register. | Positive acknowledgment when command is successfully completed. Negative acknowledgment when there is an outstanding DAS error or unacknowledged DAS reset condition. |
| Abort Scan | SDAS TAXI output disabled. SDAS beings to perform background diagnostics. (Which may be preempted by the DAS Rx.) | Positive acknowledgment when command is successfully completed. |
| Calibrate Converters | Execute converter board A/D calibration | Positive acknowledgment when command is successfully completed. Negative acknowledgment when there is an outstanding DAS error or unacknowledged DAS reset condition. |
| Query Hardware And Firmware Revisions | Gather all board ID's and revisions. Gather platform firmware ID and revision. Gather application ID and revision. Reply to query with all gathered information. | Respond with the "Hardware and Firmware Revision Query Response". The response contains the ID and revision of all SDAS boards. In addition, the reply contains firmware ID's and revisions for platform firmware and application firmware. Negative acknowledgment when there is an outstanding DAS error or unacknowledged DAS reset condition. |
| Query Detector Temperature | Gather detector temperature data. Reply to query with all gathered information. | Respond with the "Detector Temperature Query Response". The response will contain the 16-bit binary data representing the detector temperature. Negative acknowledgment when there is an outstanding DAS error or unacknowledged DAS reset condition. |
| Query SDAS Power Supplies | Gather power supply voltage data. Reply to query with all gathered information. | Respond with the "Power Supply Voltage Query Response". The response contains the 16-bit binary data representing the voltage of each power supply. Negative acknowledgment when there is an outstanding DAS error or unacknowledged DAS reset condition. |
| Query CAN Statistics | Gather CAN data. Reply to query with all gathered information. | Respond with the "CAN Statistics Query Response". The response contains the 16-bit binary data representing the CAN stats. Negative acknowledgment when there is an outstanding DAS error or unacknowledged DAS reset condition. |
| Are You There Query | Get sub-system status flags from core controller | Respond with the "Are You There Query Response". |
| Start Internal Triggers | Run the internal triggers for the specified amount of time at the specified frequency. | Positive acknowledgment when command is successfully completed. Negative acknowledgment when there is an outstanding DAS error or unacknowledged DAS reset condition. |
| DCB Data Pattern Select | Set DAS digital control board to Data Fabrication Mode. Initialize selected data pattern. | Positive acknowledgment when command is successfully completed. Negative acknowledgment when there is an outstanding DAS error or unacknowledged DAS reset condition. |
| Converter Data Pattern Select | Set DAS converter boards to Data Fabrication Mode. Initialize selected data pattern. | Positive acknowledgment when command is successfully completed. Negative acknowledgment when there is an outstanding DAS error or unacknowledged DAS reset condition. |
| DAS Seltest/ Diagnostic Select | Execute specified selftest. | Respond with the "Self-test/Diagnostic Result" command. This command contains a parameter which will indicate pass/fail status. It also contains an array of data (specific to the Diag/Test) that contains data |
| Direct Detector Setup | Write converter gain value, unaltered, to all | Positive acknowledgment when command is suc- |

TABLE 3-continued

DAS Command Response

| Command Message | SDAS Action(s) | Command Response |
|---|---|---|
| | converter boards. | cessfully completed. Negative acknowledgment when there is an outstanding DAS error or unacknowledged DAS reset condition. |
| Auto Correction Disable/Enable Mask | Using the mask value, enable or disable DAS Auto-correction circuitry as appropriate. | Positive acknowledgment when command is successfully completed. Negative acknowledgment when there is an outstanding DAS error or unacknowledged DAS reset condition. |
| Shutdown SDAS To Boot Application Mode | Gracefully shuts down all SDAS application firmware leaving boot application code running. | Positive acknowledgment when command is successfully completed. Negative acknowledgment when there is an outstanding DAS error or unacknowledged DAS reset condition. |
| Request to Download | Command decode and execution allocates RAM space large enough to hold download. | Positive acknowledgment when command is successfully completed. Negative acknowledgment when there is an outstanding DAS error or unacknowledged DAS reset condition. |
| DAS XXX Configuration File. Download of a DAS Configuration File: DCB Hardware Configuration Converter Board Address Table Macro Row Width At ISO to FET/MUX Setting Translation Table View Data Order/ Translation Table View Data Order/ Translation Table. | Download configuration file is transferred into a RMA based buffer. | Positive acknowledgment when command is successfully completed. Negative acknowledgment when there is an error in executing the command. |
| DAS Code Download. | Downloaded code is transferred into a RAM based buffer. | Positive acknowledgment when command is successfully completed. Negative acknowledgment when there is an error in executing the command. |
| Transfer Download to FLASH. | Confirm validity of downloaded file by checking its CRC. Save file in appropriate FLASH area. Check the CRC of the file in the FLASH area. Release RAM space allocated to hold download. | Positive acknowledgment when command is successfully completed. Negative acknowledgment when there is an error in executing the command. |

Interrupt generated firmware processing is set forth below in Table 4.

TABLE 4

DAS Command Response

| Interrupt | Condition | SDAS Action(s) |
|---|---|---|
| Last View | No triggers detected within the timeout period. Time out period is 2 times the view trigger period. | Initiation send of last view record (with last view magic number). |
| Trigger | Trigger received. | This interrupt is used by firmware to detect the occurrence of the first view trigger. If the first scan data view trigger is received before the first view angle s received, the scan will be aborted. Once the first view trigger interrupt is processed, this interrupt is disabled until another DAS Rx is received. |
| Trigger Jitter Error | Trigger period out of tolerance | Log trigger jitter error. |
| Parity Error | Parity Error in the detector digital signal serial stream. | Log parity error and abort scan. |
| Fault Bus | Fault Bus is asserted either by SDAS or other controller. | This interrupt is processed to platform firmware. |
| 12C Bus | There is a read request or write acknowledge by the 12C bus controller. | This event signals that the 12C bus is read for data (received or transmit). |
| CAN Bus | There is a read request or write acknowledge by the CAN bus controller. | Processed by SDAS platform firmware. |
| Exposure Enable | A change of state for the EXP_EN signal. | This interrupt is used to indicate that the exposure enable signal has changed state. At present there is no plan to use this signal in firmware. |

SDAS 42 generates the following DC voltages from the 120 VAC input source:

+24 V analog, +/-12 V analog, +/-5 V analog, +5 V digital.

All DC voltages are regulated except for the +24 V. Power cabled into SDAS 42 is unshielded and is filtered at the bulkhead without compromising the shield integrity of the enclosure. DC voltages are distributed within the SDAS using 2 connectors.

All analog power supplies share the same ground. Converter cards 104 electrically isolate the analog and digital grounds. The system chassis ground is available on one backplane connector pin. Guard rings for electrostatic discharge (ESO) protection as well as any floating metal are connected to the chassis ground. The converter board preamplifier has a separate ground connection from local analog ground for referencing the front-end integrating amplifier to the detector diode analog ground.

Figure 13:
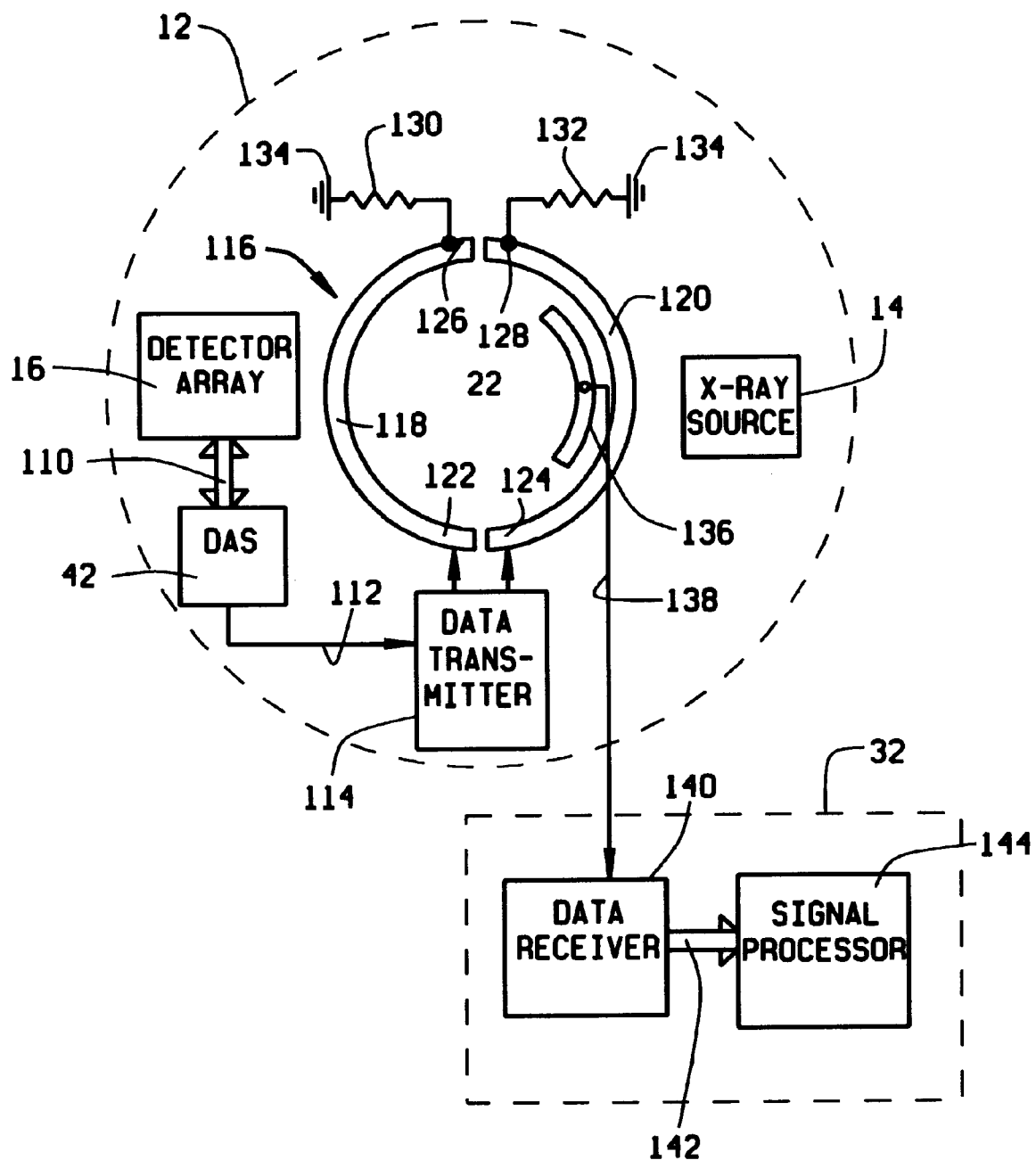
FIG. 13 is a block diagram of the slip ring.

Referring now to FIG. 13, which is a simplified, figurative schematic block diagram of gantry 12. The signals from detector array 16 are provided through lines 110 to data acquisition system (DAS) 42, which converts each signal from an analog signal format into a digital binary signal, typically, with 16 bit resolution. DAS 42 multiplexes the converted detector channel signals, together with a data clock signal and error checking signal function, into a serial digital bit signal. The serial digital bit signal is provided on lines 112 to a data signal transmitter 114 disposed on gantry 12. The data transmitter digitally encodes the serial data with an RF (radio frequency) pulse pattern, and the RF encoded signal is presented to an electromagnetic coupler, such as an RF slip ring 116 of the type disclosed in U.S. Pat. No. 5,530,424 to Harrison et al, which is assigned to the assignee of this application and which is incorporated by reference herein.

The '424 RF slip ring configuration includes one or more transmission lines disposed on the rotating side of the interface; one coupler segment mounted on the relatively stationary side. Depending on the distance between the stationary coupler and the rotating transmission line, a number of transmission line segments may be required to ensure that the coupler is always in spatial proximity to at least one of the segments to receive the electromagnetic signal. In that case each segment has a length which is a fractional portion of the arc length of the gantry's rotational path. The segments are cascaded, end-to-end around the gantry's rotational axis, typically along the circumference of the aperture 22 such that the aggregate length provides a substantially 360° arc, i.e. a full rotation of the gantry. Two transmission line segments 118, 120 are used and are mounted in a manner to provide adjacent positioning of first ends 122, 124 and second ends 126, 128 of transmission lines 118, 120, respectively. Contiguous placement of the ends of each of the transmission lines provides substantial continuity of the electromagnetic coupling along the full rotational path of the gantry.

Data transmitter 114 provides the encoded serial data to first ends 122, 124 of each of the transmission lines 118,120. Second ends 126, 128 of each transmission line are connected through terminal impedance's 130, 132 to signal ground 134. A coupler element 136 positioned on the stationery frame in a manner to ensure physical proximity of the coupler to one and both of the transmission lines 118, 120 during gantry rotation. The encoded data is electromagnetically coupled through to coupler 136, as described in the hereinbefore incorporated '424 patent to Harrison et al. On the stationery frame side, the coupled data signal is provided on lines 138 to SRU 32. The encoded data is received at a data signal receiver 140. As described in detailed hereinafter with respect to FIG. 16, signal receiver 140 decodes the serial data using a rules based algorithm and provides the decoded data through lines 142 to a signal processor 144. Signal processor 144 includes signal memory (not shown) for storing the program algorithms which govern the CT processing of the received data in response to operator commands. The algorithms and the resulting processes are well known in the art. In this manner, signal processor 144 collates the decoded image data sets into a composite view associated with the particular angular position of the gantry.

Figure 14:
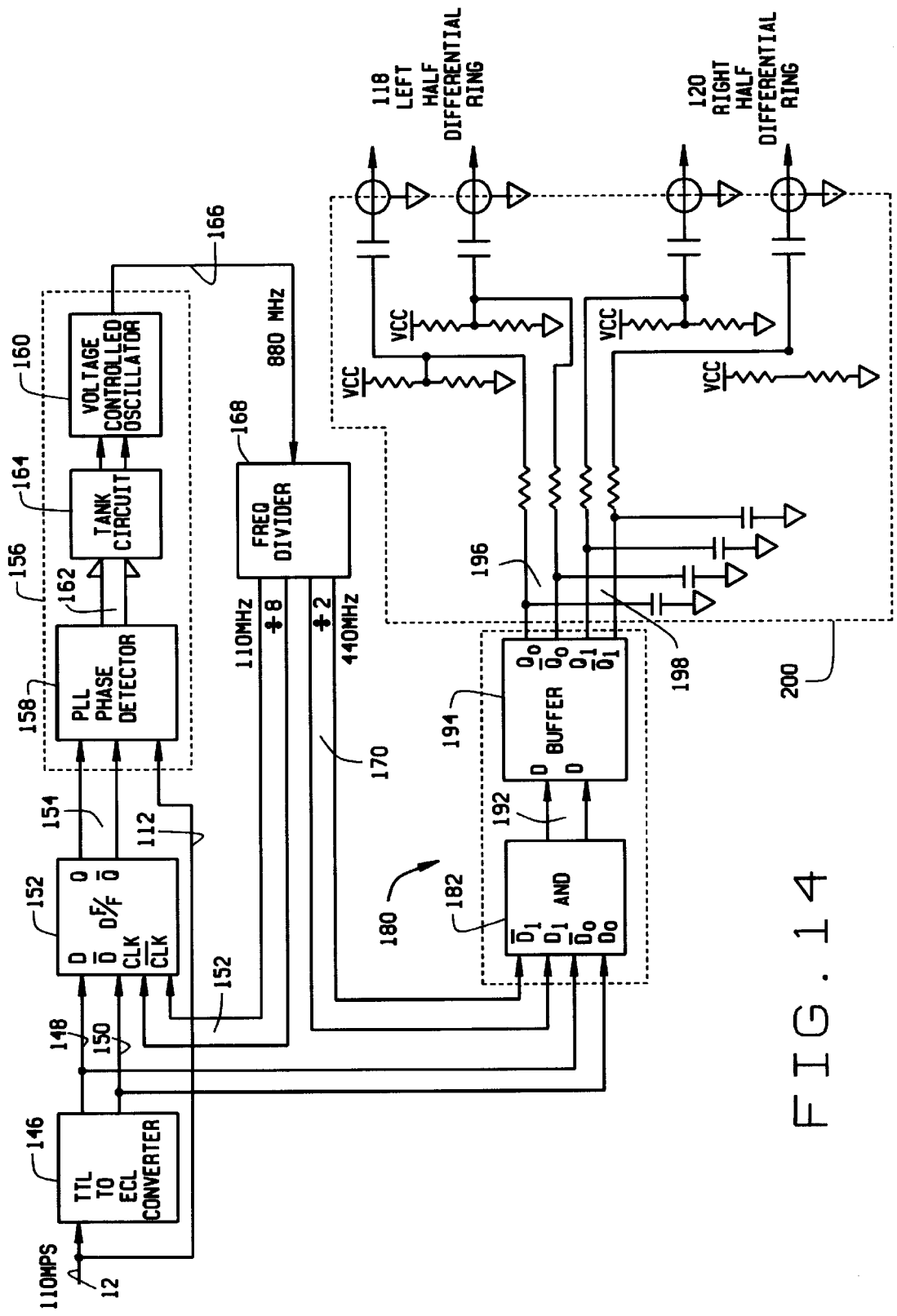
FIG. 14 is a more detailed block diagram of the slip ring.

Referring now to FIG. 14, the serial data signal on lines 112 from DAS 42 is received at an approximate bit signal speed of 110 Mbps. The DAS data is in $T^2L$ (transistor-transistor-logic) format. At the bit signal speeds involved, the substitution of RF amplitude modulation of the data with RF digital encoding requires high speed digital circuitry. Therefore, signal transmitter 114 and signal receiver 140 each comprises digital gate logic functions which are implemented with emitter coupled logic (ECL) devices. The ECL devices may be single gate devices, with gate switching speeds of 250 pico seconds and flip-flop toggling at over 2 Ghz. These devices, which are available from various vendors, including MOTOROLA, Inc. as their ECLinPS Lite (a trademark of MOTOROLA, Inc.), provide high switched speed, single gate devices in small (standard 8 lead SOIC) packages with half the propagation delay of the multi-gate, 28 pin configurations. These characteristics, together with the lower signal switching amplitudes (typical 800 mV output swing into a specified 50 ohm load) provide the necessary bandwidth for the present RF encoding process.

In FIG. 14, the $T^2L$ format data signal from DAS 42 is presented to a $T^2L$-to-ECL converter 146 and the output ECL formatted data signal (Q and the convolute Q-NOT is provided on lines 148, 150 respectively to D and D-NOT inputs, respectively, of a D edge flip-flop ("flop") 152, such as the MOTOROLA ECL Differential Data and Clock flip-flop, model MC10EL52. Flop 152 is clocked with a 110 Mhz taxi clock signal provided on lines 152 (CLK and CLK-NOT). The flop data output is presented on lines 154 to a phase locked loop (PLL) 156 which includes a Phase-Frequency Detector 158 (detector), such as the MOTOROLA model MC12040, and a voltage controlled oscillator (VCO) 160, such as the MOTOROLA model MC12148. Detector 158 also receives the DAS data signal on line 112 and determines the presence of a signal phase difference between the two. A phase difference is quantified as a duty cycle pulse provided on output lines 162 through a tank (resistor capacitor) circuit 164 to a voltage controlled oscillator (VCO) 160.

VCO 160 provides an output clock signal at a nominal, center frequency which is adjusted upwardly or downwardly based on the magnitude of the phase error signal provided from detector 158. In one embodiment, the DAS data signal speed is 110 Mbps and, as described hereinafter, the RF encoding frequency is chosen to be 4x the data signal speed, or 440 Mhz. Therefore, the VCO center frequency is selected at 880 Mhz, or approximately eight times the DAS serial data bit speed. The 880 Mhz clock signal is provided on lines 166 to a frequency divider 168, such as the MOTOROLA MC10EL34 Clock Generation Chip which provides a divide by eight 110 Mhz taxi clock signal on line 152, and a divide by two 440 Mhz RF encoding signal on lines 170. The PLL 156 ensures that each of these signals are phase synchronized to the DAS data signal to synchronize the data signal bit edges to prevent overlap or underlap of adjacent bits which can produce image jitter.

The serial bit data signal is encoded in a digital pattern at RF carrier signal frequency, which is decoded on the receiver side to restore the signal to its original logic state. This RF encoding carrier signal allows for electromagnetic coupling through the RF slip ring and the digital encoding provides high noise discrimination as well as a simpler, lower cost RF modulating scheme. In one embodiment, only one of the two logic states of the serial data signal are encoded. If a first logic state is chosen as the encoded state then, on the receiver side, the absence of encoding implies the presence of the second logic state. Also, to simplify the encoding process in a best mode embodiment, a serial pulsed signal is chosen, which provides a known number of pulses, at a given pulse width and RF pulse repetition frequency (PRF), within the bit time interval of the encoded signal bit.

Figure 15:
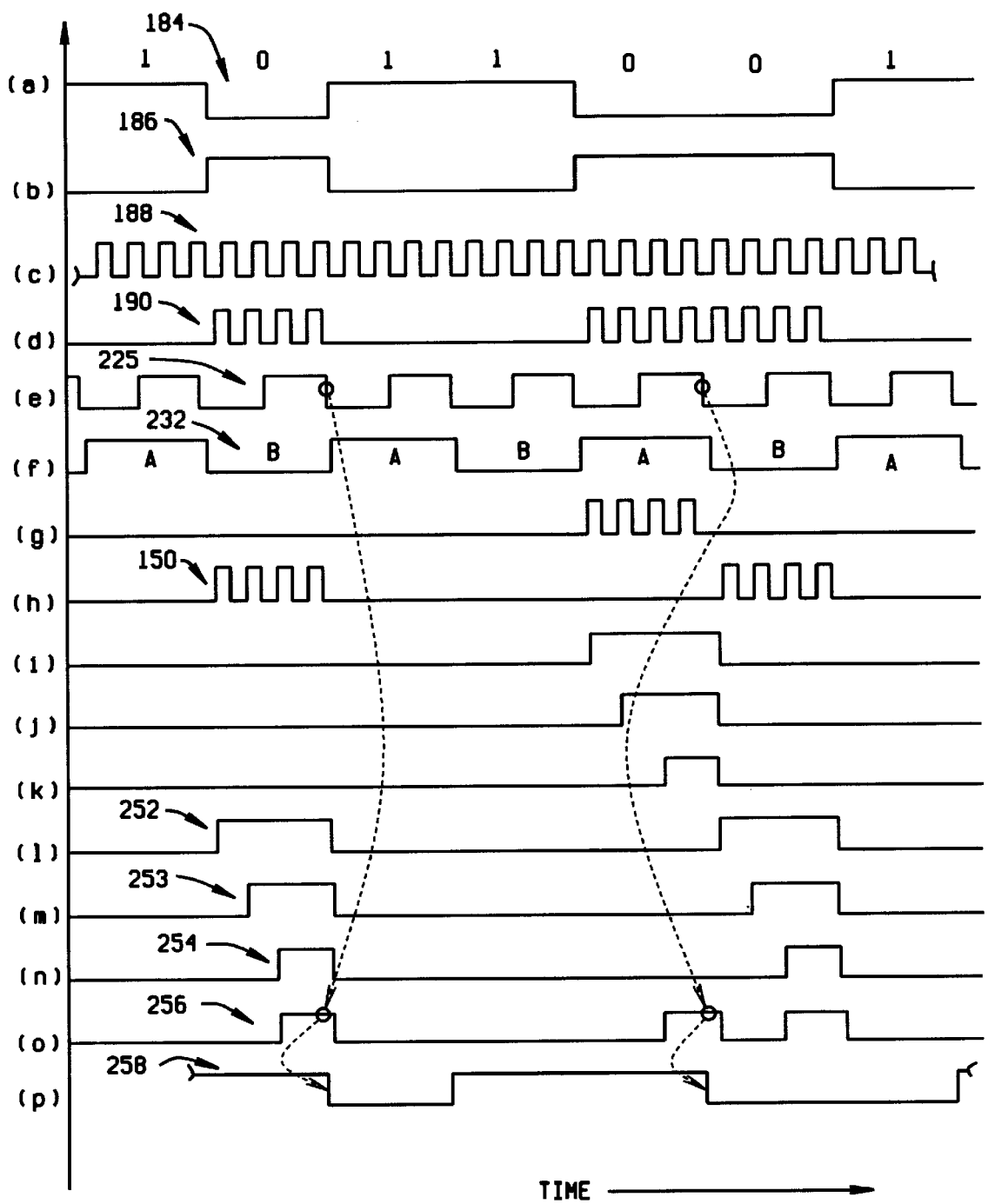
FIG. 15 is a signal waveform referenced in connection with FIGS. 14 and 16.

Encoding circuit 180, which in one embodiment is an AND function, such as the MOTOROLA model MC10EL05 "2 input Differential AND/NAND" gate, which receives the ECL serial bit data signal on lines 148, 150 at the $D_0$-NOT and $D_0$ inputs of the gate. The logic zero state of the data signal is the bit state chosen for encoding, and the DATA-NOT (the inverse of the data signal) is presented to the $D_0$ input of the gate. The AND gate also receives the modulating signal on lines 170 from frequency divider 168 at the $D_1$-NOT and $D_1$ inputs of the gate. Referring to FIG. 15, illustration (a) illustrates a 1011001 excerpt of the DATA signal waveform 184, illustration (b) is the corresponding DATA-NOT segment waveform 186, and illustration (c) is the 440 Mhz modulating signal waveform 188. The gate 182 ANDs the modulating signal with the DATA-NOT signal to provide the corresponding encoded pattern waveform 190 in FIG. 15, illustration (d).

In addition to the serial pulse pattern providing a simple scheme to implement, it also provides a simple pattern from which to detect noise interference. The encoded signal is presented on output lines 192 from the AND gate to a buffer 194, such as a MOTOROLA Differential Fanout Buffer, model MC10EL11. With the two transmission line segments of the RF slipring of the present embodiment, the buffer 114 provides a pair of differential, identical, encoded serial data signal on lines 116 and 118 through a resistor-capacitor impedance matching/filter circuit 120 to the inputs 40, 41 of the left half transmission line segment 36 and right half transmission line segment 38. The differential RF encoded data signal is coupled through the RF slip ring as described in the incorporated U.S. Pat. No. 5,530,424 to Harrison et al, received by the slip ring coupler 136, and presented on lines 138 to data receiver 140.

Figure 16:
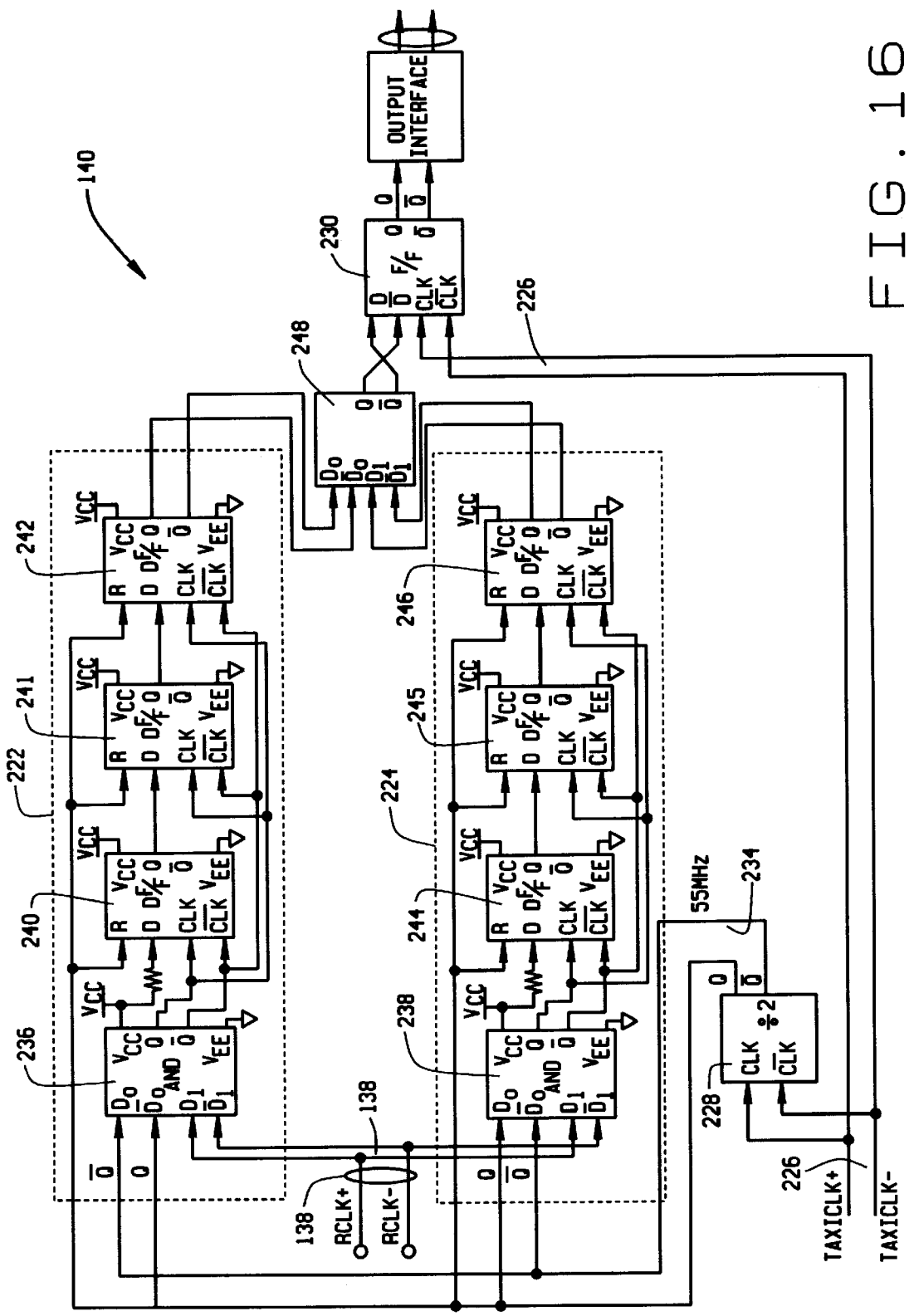
FIG. 16 is a schematic illustration of the data receiver shown in FIG. 13.

Referring now to FIG. 16, receiver 140 receives the encoded data signal at the input of each of a pair of decoding circuits 222, 224. For descriptive purposes the pair of decoding circuits 222, 224 are referred to as Channel A and Channel B, respectively. Clock recovery circuitry (not shown) recovers the taxi clock signal which is shown by the waveform 225 in FIG. 15, illustration (e), and which is presented on lines 226 to a divide by 2 circuit 228 and, inverted, to the CLK-NOT input of a final reclock flip-flop 230.

The use of A and B channels facilitates the 9.2 nano second bit interval of the 110 Mbps data signal by alternating the decoding task on succeeding bit intervals. Therefore, each channel decodes only one of two succeeding giving each channel a cycle time of 18.4 nano seconds. The channels are enabled and disabled by a SELECT channel signal provided by divider circuit 228 at one-half (i.e. 55 Mhz) the (110 Mhz) taxi clock frequency. The SELECT signal, which is shown by the waveform 232 in FIG. 15, illustration (f), is synchronized to the data signal through synchronization of the taxi clock by the PLL 82 in signal transmitter 114, and is presented (Q and Q-NOT) on lines 234 to the $D_0$ and $D_0$-NOT inputs of AND gates 236, 238 of the A and B channels, respectively.

The A and B channels each include the first element AND gates 236, and 238, followed by cascaded D edge triggered flip-flops 240–242 and 244–246, respectively. The differential Q output of the last flip-flops 242 and 246 are presented to the $D_0$ and $D_1$ inputs of AND gate 248. These AND gates and D flip-flops are the same type ECL gates described hereinbefore with respect to the signal transmitter diagram of FIG. 14. The AND gates 236, 238 are held LOW (logic zero state), which is disabled, whenever the $D_0$ input is HIGH. Therefore, the SELECT Q signal is presented to the Do input of AND 238 and the SELECT Q-NOT is presented to the $D_0$ of AND 236. This allows the alternate toggling of the channels, which is functionally shown in the SELECT signal waveform 232 (FIG. 15, illustration (f)) with alternate states of the waveform labeled A and B. Referring to FIG. 15, illustration (d), the occurrence of the first series of four pulses, corresponding to the logic zero state of the data signal waveform 184 in illustration (a), is decoded by the channel B decoding logic 224 with the LOW state of the SELECT Q waveform 232 (illustration (f)).

With a LOW Do input to the AND gate 238, the gate Q output follows the encoded data signal to provide the four pulse output shown in waveform 250 of FIG. 15, illustration (h). The AND gate Q output is presented to the CLK inputs of each of the D flip-flops 244–246, causing each to toggle HIGH in succession on the first three of the data signal's four pulses, as shown by the waveforms 252–254 of illustrations (l) through (n). The third pulse also sets the output of the AND gate 248 HIGH, as shown by the waveform 256 of FIG. 15, illustration (o). The Q and Q-NOT outputs of gate 248 are inversely presented to the D-NOT and D inputs, respectively, of the output D flip-flop 230, which also receives the taxi clock signal (waveform 208, FIG. 15, illustration (c)) at its CLK-NOT input.

With the Q output of the gate 248 HIGH, the Q-NOT is LOW, setting the D input to the flop 230 LOW. On the next LOW to HIGH transition of the CLK-NOT input (the HIGH to LOW transistion of the taxi clock signal waveform 108 of FIG. 15, illustration (c)), flop 230 transitions LOW. With the LOW to HIGH transistion of the SELECT signal (232, FIG. 15, illustration (f)) the AND gate 248 goes LOW and on the next LOW to HIGH transition of the taxi clock-NOT, which corresponds to one bit interval of the data signal, the Q output of the flop 230 goes high. The output of flop 230, i.e. the reclock signal, is the decoded data signal, as shown by the waveform 258 of FIG. 15, illustration (p). Comparing FIG. 15 illustration (a) with illustration (p) it is seen that the decoded signal replicates the rotating frame data signal, with a one bit interval shift, i.e. one taxi clock period.

Similarly, the decoding circuitry decodes the absence of pulses as logic one bit states. With the appearance of the second pulse group in waveform 110, a "00", the SELECT signal enables the decode circuitry 222 for the first bit interval of pulses and enables circuitry 224 for the second group of four pulses. Each of these encoded bits is decoded in the same manner as described hereinabove.

In one embodiment, the encoding algorithm is simplified by the use of a limited number of pulses and a simple rules based decoding algorithm which requires a simple majority for translating the received pulses into a logic zero. Three pulses occurring within a bit interval is translated as a logic zero and less than three as a logic one. This is based on empirical observations of the signal noise characteristics of a CT rotating interface. A four pulse encoding pattern is found to be sufficient in ensuring the integrity of the coupled data in its transfer across the CT rotating interface. However, it should be understood that greater or lesser numbers of pulses may be used, as well as greater complexity pulse patterns and decoding algorithms, as may be deemed necessary by those skilled in the art for a particular application. Also, the signal transmitter and signal receiver may be altered or completely reconfigured as necessary to achieve the various encoding patterns and decoding algorithms that may be used.

Many variations and additions to the above described exemplary system can be made. For example, a graphic based user interface which enables the user to easily prescribe multislice scan and image reconstruction in various forms with, for example, optimum table speed, x-ray beam collimation, data collection slice thickness, x-ray beam voltage and current values, as well as the reconstruction method to obtain the desired image quality. Such an interface may be activated by a touch screen, voice, or other known interface methodologies that are easy to use and understand. The host computer can be preprogrammed to include various default modes based upon the type of scan being performed to further simplify the operator performed selections.

Again, the above described multislice CT system can be used to collect one, two or more slices of data to provide enhanced flexibility. Such system also enables fast scanning speed with good image quality and z-axis resolution, with a low x-ray tube load. Further, and using the system, the operator can easily and quickly prescribe multislice scan and image reconstruction parameters.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

We claim:

1. A data acquisition system for a scalable imaging system including a detector, said data acquisition system comprising:
   a backplane;
   a plurality of converter cards configured to receive analog signals from the detector and to couple to said backplane, each of said converter cards comprising an analog to digital converter.

2. A data acquisition system in accordance with claim 1 wherein said system is reconfigurable by adding and removing converter cards.

3. A data acquisition system in accordance with claim 1 wherein said backplane further comprises connectors for receiving inputs from the detector.

4. A data acquisition system in accordance with claim 1 wherein each said converter card serves one slice of data.

5. A data acquisition system in accordance with claim 1 further comprising a serial data transmission bus, each of said converter cards coupled to said bus.

6. A data acquisition system in accordance with claim 1 wherein the imaging system further includes a slip ring and said data acquisition system further comprises a translation and transmission unit for transmitting data from said converter cards to the slip ring.

7. A data acquisition system in accordance with claim 1 further comprising a sub-system control for controlling operation of said converter cards, and a detector control coupled to said sub-system control for controlling operation of the detector.

8. A data acquisition system in accordance with claim 1 wherein each of said converter cards further comprises an anti-aliasing filter coupled to an input of said analog to digital converter.

9. A data acquisition system in accordance with claim 1 wherein each of said converter cards further comprises a selectable multi-gain "boxcar" integrating amplifier, a sample/hold unit, and an output channel multiplexer.

10. A data acquisition system in accordance with claim 1 wherein said system is configured to perform system diagnostic functions.

11. A multislice imaging system comprising a detector and a scalable data acquisition system coupled to said detector, said scalable data acquisition system configured to control operation of said detector and to convert signals received from the detector to digital form.

12. A system in accordance with claim 11 wherein said scalable data acquisition system is further configured to selectively gang signals received from said detector.

13. A system in accordance with claim 11 wherein said data acquisition system is reconfigurable by adding and removing converter cards.

14. A system in accordance with claim 11 wherein said scalable data acquisition system comprises a backplane and a plurality of converter cards configured to receive the analog signals from the detector, each of said converter cards comprising an analog to digital converter.

15. A system in accordance with claim 14 wherein said detector is coupled to said data acquisition system by a plurality of flex cables, each of said flex cables connected to said backplane.

16. A system in accordance with claim 11 wherein each said converter card serves one slice of data.

17. A system in accordance with claim 11 further comprising a serial data transmission bus, each of said converter cards coupled to said bus.

18. A system in accordance with claim 11 further comprising a slip ring, said data acquisition system further comprising a translation and transmission unit for transmitting data from said converter cards to said slip ring.

19. A system in accordance with claim 11 wherein said data acquisition system further comprises a sub-system control for controlling operation of said converter cards, and a detector control coupled to said sub-system control for controlling operation of the detector.

20. A system in accordance with claim 11 wherein each of said converter cards further comprises an anti-aliasing filter coupled to an input of said analog to digital converter.

21. A system in accordance with claim 11 wherein each of said converter cards further comprises a selectable multi-gain "boxcar" integrating amplifier, a sample/hold unit, and an output channel multiplexer.

22. A system in accordance with claim 11 wherein said data acquisition system is configured to perform system diagnostic functions.

23. A data acquisition system for a scalable imaging system including a detector and a slip ring, said data acquisition system comprising:
   a backplane;
   a plurality of converter cards configured to receive analog signals from the detector and to couple to said backplane, each of said converter cards comprising an analog to digital converter and configured to serve one slice of data; and
   a translation and transmission unit for transmitting data from said converter cards to the slip ring.

24. A data acquisition system in accordance with claim 23 wherein said system is reconfigurable by adding and removing converter cards.

25. A data acquisition system in accordance with claim 23 wherein said backplane further comprises connectors for receiving inputs from the detector, and wherein channels of at least one converter card are interweaved with detector cells assignments.

26. A data acquisition system in accordance with claim 23 further comprising a serial data transmission bus, each of said converter cards coupled to said bus.

27. A data acqaisition system in accordance with claim 23 further comprising a sub-system control for controlling operation of said converter cards, and a detector control coupled to said sub-system control for controlling operation of the detector.

28. A data acquisition system in accordance with claim 23 wherein each of said converter cards further comprises an anti-aliasing filter coupled to an input of said analog to digital converter.

29. A data acquisition system in accordance with claim 23 wherein each of said converter cards further comprises a selectable multi-gain "boxcar" integrating amplifier, a sample/hold unit, and an output channel multiplexer.

30. A data acquisition system in accordance with claim 23 wherein said system is configured to perform system diagnostic functions.

* * * * *